United States Patent [19]
Chen

[11] Patent Number: 5,994,093
[45] Date of Patent: Nov. 30, 1999

[54] DETECTION AND CORRECTION OF ABNORMALITIES OF CELLS HAVING DECREASED LEVEL OF GLYCINE N-METHYLTRANSFERASE

[76] Inventor: Yi-Ming A. Chen, No. 21, Alley 14, Lane 16, Sec. 1, Chung Cheng Rd., Taipei, Taiwan

[21] Appl. No.: 08/907,492

[22] Filed: Aug. 8, 1997

[51] Int. Cl.[6] ...................................................... C12Q 1/48
[52] U.S. Cl. ............................................. 435/15; 435/193
[58] Field of Search ............................. 435/15, 193, 325, 435/370

[56] References Cited

U.S. PATENT DOCUMENTS 5,814,505  9/1998  Matsukawa et al. .................... 435/193

OTHER PUBLICATIONS

Raha, A., et al. (1994) J. Biol. Chem. 269(8), 5750–5756.

Raha, A., et al. (1995) Arch. Biochem. Biophys. 322(2), 395–404.

*Primary Examiner*—Charles L. Patterson, Jr.
*Attorney, Agent, or Firm*—Bacon & Thomas

[57] ABSTRACT

The present invention relates to a method of detecting abnormalities of cells having decreased level of Glycine N-methyltransferase (GNMT) and to a method of correcting the abnormalities of cells.

3 Claims, 11 Drawing Sheets

(1 of 11 Drawing Sheet(s) Filed in Color)

```
 -10 GGCACGAGGGATGGTGGACAGCGTGTACCGGACCCGCTCCCTGGGGGTGGCGGCCGAAGG      50
   1              M  V  D  S  V  Y  R  T  R  S  L  G  V  A  A  E  G   17

51 GCTCCCGGACCAGTACGCGGACGGGGAGGCGGCGCGCGTGTGGCAGCTGTATATCGGAGA     110
  18  L  P  D  Q  Y  A  D  G  E  A  A  R  V  W  Q  L  Y  I  G  D     37

121 CACCCGCAGCCGCACCGCCGAGTACAAGGCATGGCTGCTTGGGCTGCTGCGCCAGCACGG     170
  38  T  R  S  R  T  A  E  Y  K  A  W  L  L  G  L  L  R  Q  H  G     57

171 CTGCCAGCGGGTGCTCGACGTAGCCTGTGGCACTGGGGTGGACTCCATTATGCTGGTGGA     230
  58  C  Q  R  V  L  D  V  A  C  G  T  G  V  D  S  I  M  L  V  E     77

231 AGAGGGCTTCAGTGTGACGAGTGTGGATGCCAGTGACAAGATGCTGAAGTATGCACTTAA     290
  78  E  G  F  S  V  T  S  V  D  A  S  D  K  M  L  K  Y  A  L  K     97

291 GGAGCGCTGGAACCGGCGGCACGAGCCCGCCTTCGACAAGTGGGTCATCGAAGAAGCCAA     350
  98  E  R  W  N  R  R  H  E  P  A  F  D  K  W  V  I  E  E  A  N    117

351 CTGGATGACTCTGGACAAAGATGTGCCCCAGTCAGCAGAGGGTGGCTTTGATGCTGTCAT     410
 118  W  M  T  L  D  K  D  V  P  Q  S  A  E  G  G  F  D  A  V  I    137

411 CTGCCTTGGAAACAGTTTCGCTCACTTGCCAGACTGCAAAGGGGACCAGAGTGAGCACCG     470
 138  C  L  G  N  S  F  A  H  L  P  D  C  K  G  D  Q  S  E  H  R    157

471 GCTGGCGCTGAAAAACATTGCGAGCATGGTGCGGGCAGGGGGCCTACTGGTCATTGATCA     530
 158  L  A  L  K  N  I  A  S  M  V  R  A  G  G  L  L  V  I  D  H    177

531 TCGCAACTACGACCACATCCTCAGTACAGGCTGTGCACCCCCAGGGAAGAACATCTACTA     590
 178  R  N  Y  D  H  I  L  S  T  G  C  A  P  P  G  K  N  I  Y  Y    197

591 TAAGAGTGACTTGACCAAGGACGTCACAACATCAGTGCTGATAGTGAACAACAAGGCCCA     650
 199  K  S  D  L  T  K  D  V  T  T  S  V  L  I  V  N  N  K  A  H    217

651 CATGGTGACCCTGGACTATACGGTGCAGGTGCCGGGGGCTGGCCAGGATGGCTCTCCTGG     710
 218  M  V  T  L  D  Y  T  V  Q  V  P  G  A  G  Q  D  G  S  P  G    237

711 CTTGAGTAAGTTCCGGCTCTCCTACTACCCACACTGTCTGGCATCCTTCACGGAGCTGCT     770
 238  L  S  K  F  R  L  S  Y  Y  P  H  C  L  A  S  F  T  E  L  L    257

771 CCAAGCAGCCTTCGGAGGTAAGTGCCAGCACAGCGTCCTGGGCGACTTCAAGCCTTACAA     830
 258  Q  A  A  F  G  G  K  C  Q  H  S  V  L  G  D  F  K  P  Y  K    277

831 GCCAGGCCAAACCTACATTCCCTGCTACTTCATCCACGTGCTCAAGAGGACAGACTGAGT     890
 278  P  G  Q  T  Y  I  P  C  Y  F  I  H  V  L  K  R  T  D         295

891 GTGGCCTCAGCTCCCACAAGCCTCTGCCCAGGCACTGCTAGGCTCTGTCTGGAAGATGGG     950

951 GACCAGCAGCCCCACACCAGGGCCAGCCTCTAGAGCAGACTACAGCTGGGGTGCAGGGAT    1010

1011 GTGGGTTCCACAGACGGAAGGGTAAACAATATAGTCTTTTTCAGTTCCTGCAAAAAAAAA    1070

1071 AAAAAAAAAAAAAAAAAA                                              1087
```

```
     ****  *  ****  **  *   *    *  *  ****    *   *  *****      **   *  *   *
  1  GGCACGAGGAACAGCAGTTGAACATGGGTCAGTCGGTCCTGAGAGATGGGCGAGCGCCGT      60
  1                           M  G  Q  S  V  L  R  D  G  R  A  P      12
     *  ** *                     *
 61  TCCGAAGGCTCCCGGACCAGTACGCGGACGGGGAGGCGGCGCGCGTGTGGCAGCTGTATA     120
 13  F  R  R  L  P  D  Q  Y  A  D  G  E  A  A  R  V  W  Q  L  Y      32

121  TCGGAGACACCCGCAGCCGCACCGCCGAGTACAAGGCATGGCTGCTTGGGCTGCTGCGCC     180
 33  I  G  D  T  R  S  R  T  A  E  Y  K  A  W  L  L  G  L  L  R      52

181  AGCACGGCTGCCAGCGGGTGCTCGACGTAGCCTGTGGCACTGGGGTGGACTCCATTATGC     240
 53  Q  H  G  C  Q  R  V  L  D  V  A  C  G  T  G  V  D  S  I  M      72

241  TGGTGGAAGAGGGCTTCAGTGTGACGAGTGTGGATGCCAGTGACAAGATGCTGAAGTATG     300
 73  L  V  E  E  G  F  S  V  T  S  V  D  A  S  D  K  M  L  K  Y      92

301  CACTTAAGGAGCGCTGGAACCGGCGGCACGAGCCCGCCTTCGACAAGTGGGTCATCGAAG     360
 93  A  L  K  E  R  W  N  R  R  H  E  P  A  F  D  K  W  V  I  E     112

361  AAGCCAACTGGATGACTCTGGACAAAGATGTGCCCCAGTCAGCAGAGGGTGGCTTTGATG     420
113  E  A  N  W  M  T  L  D  K  D  V  P  Q  S  A  E  G  G  F  D     132

421  CTGTCATCTGCCTTGGAAACAGTTTCGCTCACTTGCCAGACTGCAAAGGGGACCAGAGTG     480
133  A  V  I  C  L  G  N  S  F  A  H  L  P  D  C  K  G  D  Q  S     152

481  AGCACCGGCTGGCGCTGAAAAACATTGCGAGCATGGTGCGGGCAGGGGGCCTACTGGTCA     540
153  E  H  R  L  A  L  K  N  I  A  S  M  V  R  A  G  G  L  L  V     172

541  TTGATCATCGCAACTACGACCACATCCTCAGTACAGGCTGTGCACCCCCAGGGAAGAACA     600
173  I  D  H  R  N  Y  D  H  I  L  S  T  G  C  A  P  P  G  K  N     192

601  TCTACTATAAGAGTGACTTGACCAAGGACGTCACAACATCAGTGCTGATAGTGAACAACA     660
193  I  Y  Y  K  S  D  L  T  K  D  V  T  T  S  V  L  I  V  N  N     212

661  AGGCCCACATGGTGACCCTGGACTATACGGTGCAGGTGCCGGGGGCTGGCCAGGATGGCT     720
213  K  A  H  M  V  T  L  D  Y  T  V  Q  V  P  G  A  G  Q  D  G     232
                                 *
721  CTCCTGGCTTGAGTAAGTTCCGGCTCTCCTACTACCCACACTGTCTGGCATCCTTCACGG     780
233  S  P  G  L  S  K  F  R  L  S  Y  Y  P  H  C  L  A  S  F  T     252

781  AGCTGCTCCAAGCAGCCTTCGGAGGTAAGTGCCAGCACAGCGTCCTGGGCGACTTCAAGC     840
253  E  L  L  Q  A  A  F  G  G  K  C  Q  H  S  V  L  G  D  F  K     272
            *  *
841  CTTACAAGCCAGGCCAAACCTACATTCCCTGCTACTTCATCCACGTGCTCAAGAGGACAG     900
273  P  Y  K  P  G  Q  T  Y  I  P  C  Y  F  I  H  V  L  K  R  T     292

901  ACTGAGTGTGGCCTCAGCTCCCACAAGCCTCTGCCCAGGCACTGCTAGGCTCTGTCTGGA     960
293  D

961  AGATGGGGACCAGCAGCCCCACACCAGGGCCAGCCTCTAGAGCAGACTACAGCTGGGGTG    1020

1021 CAGGGATGTGGGTTCCACAGACGGAAGGGTAAACAATATAGTCTTTTTCAGTTCCTGAAA    1080

1081 AAAAAAAAAAAAAAAAAAAAAAAAAAAAAAAAA                               1113
```

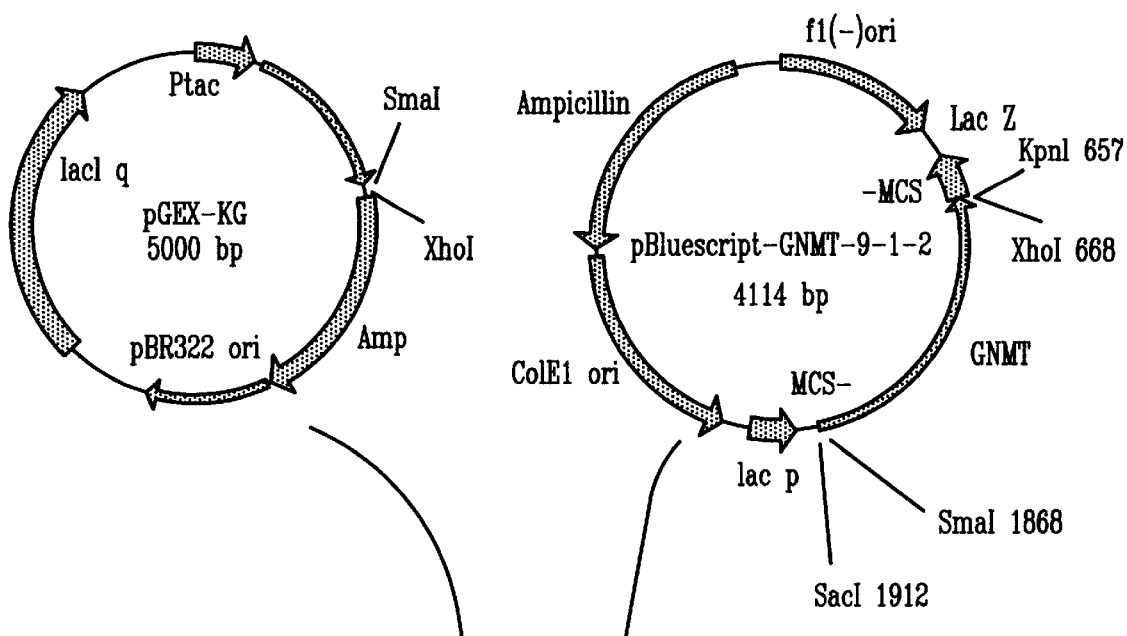
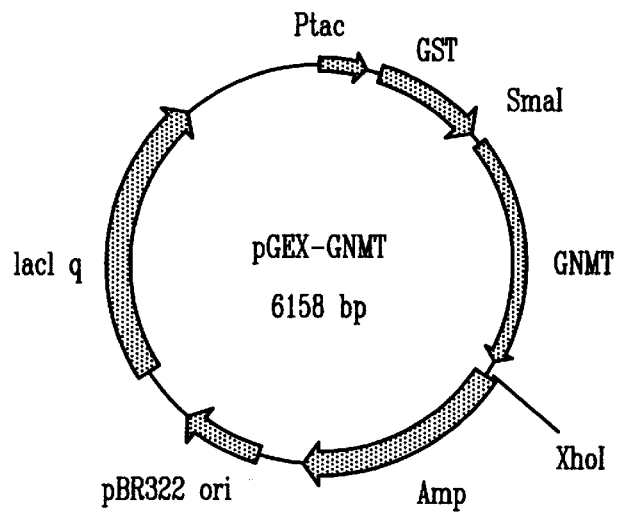
Figure 5

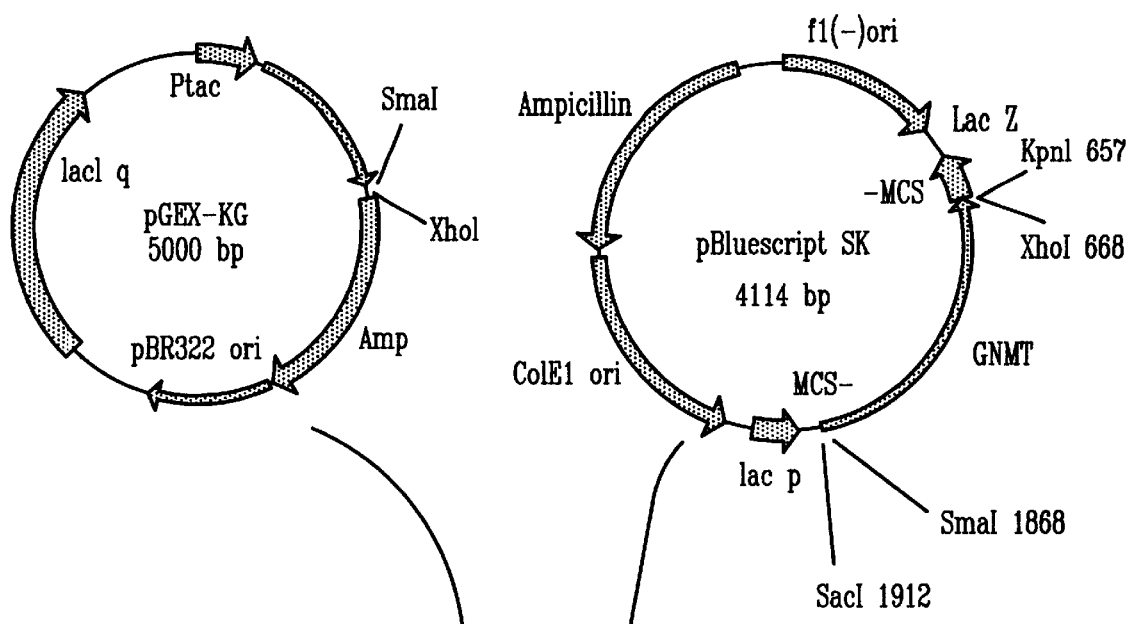
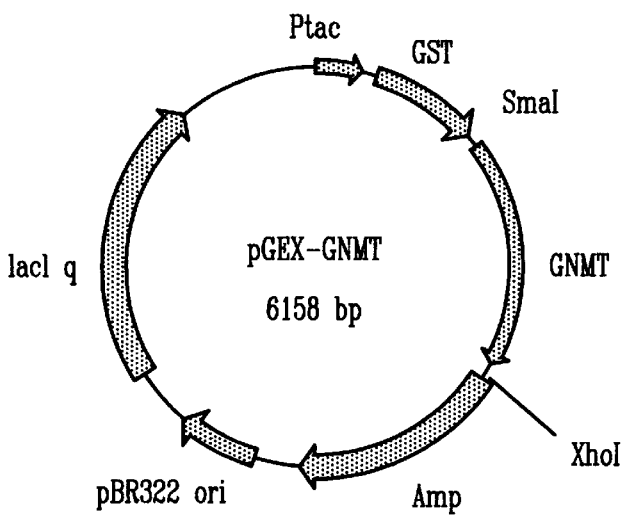
Figure 8

DETECTION AND CORRECTION OF ABNORMALITIES OF CELLS HAVING DECREASED LEVEL OF GLYCINE N-METHYLTRANSFERASE

BACKGROUND OF THE INVENTION

The present invention relates to a method of detecting abnormalities of cells having decreased level of Glycine N-methyltransferase (GNMT) and to a method of correcting the abnormalities of cells.

One of the most common types of human diseases throughout the world due to cell abnormalities is cancer, which is also the leading cause of death nowadays. Cancers are fully developed (malignant) tumors with a specific capacity to invade and destroy the underlying mesenchyme, i.e., local invasion. In some cases, invading tumor cells may further penetrate lymphatic vessels or blood vessels newly formed in the tumor and then may be carried to local lymph nodes or even to distant organs where they may produce secondary tumors (metastases). Tumors are usually recognized by the fact that the cells, which may arise from any tissue, are no longer responsive to at least some normal growth controlling mechanisms and hence show abnormal growth. Apart from the cancer, a tumor may merely develop locally and never become malignant, i.e., a benign tumor. Alternatively, cells of a tumor may merely have morphological appearances of cancer cells but remain in their place, i.e., an in situ tumor, although in this case the tumor may sometimes precede a cancer in situ.

There are no absolute methods for diagnosing or assessing the degree of malignancy of tumors. However, among the methods, microscopic examination of tissue is still the most reliable method for routine use. In a pathologic study, tumors can be graded by making an approximate assessment of the degree of structural dedifferentiation (anaplasia) based on histological and cytological criteria by microscopically examining sections thereof. However, on one hand, some cells may have lost their specific structural characters but still retain differentiated biochemical features, while others may still appear differentiated in structure but have lost many normal function attributes. On the other hand, a tumor is not homogeneous and may contain areas with more than one tumor grade, therefore, a developed tumor may consist of a mixed population of cells which may differ in structure, function, growth potential, resistance to drugs or X-rays and ability to invade and metastasize. The two limitations reduce the effectiveness of histological examination of tumors. In another aspect, such an examination by sampling specimens is not suitable for investigations on a large scale.

Many attempts to find absolute markers of malignancy have long been made. Other attempts to identify tumor-specific or tumor-associated proteins, either by direct measurement or by developing specific antibodies to these proteins, are still being made at the moment. They seem to be promising approaches not only in diagnosis but also in providing strategies of destroying cancer cells. A variety of substances wherein the presence or concentrations thereof in vivo may be indicative for certain cancers have been reported, such as oncofetal antigens, e.g., alpha-fetoprotein; serum proteins, e.g., ferritin; enzymes; polyamines; ectopic hormones; cell markers; receptors or tumor-associated viral antigens. However, the most commonly used method of diagnosis of cancers depends on histology rather than any of the above substances. The lack of any absolute markers is a major deficiency in studying cancer.

Recent observations provide some contemplations in searching for the substances intimately associated with carcinogenesis. Cancer is appreciated as a result of multiple gene aberrations which cause both the activation of oncogenes and inactivation of tumor suppressor genes. Further, the differential expression of those critical genes associated with oncogenesis is able to be reflected at the messenger RNA (mRNA) level in cells. For effectively screening the altered ones of interest amongst a great amount of mRNA, a powerful tool, i.e., differential display, has been established to identify and isolate a small subset of genes which are differentially expressed between tumorous and normal cells (Liang et al., Cancer Research 52, 6966–6968, 1992).

It is surprisingly found in the present invention that the GNMT gene is differentially expressed between normal and tumorous cells with a significant distinction. An objective of the present invention is to provide a method of detecting abnormalities of cells by determining the relative levels of gene expression of GNMT. Furthermore, another objective of the present invention is to provide a method of correcting the abnormalities of cells by delivering GNMT into the abnormal cells.

SUMMARY OF THE INVENTION

The present invention provides a method of detecting abnormalities of cells having decreased level of GNMT. The present inventions further provides a method of correcting the abnormalities of cells.

In an embodiment of the present invention, the method differential display was applied to identify possible genes which are differentially expressed between tumorous and normal hepatic cells and then a cDNA fragment with differential expression was isolated, which was determined to be part of the GNMT gene. The full-length cDNA fragments of GNMT were obtained after screening a cDNA library and then the sequences thereof were determined.

In one aspect, the present invention includes those full-length cDNA fragments of GNMT obtained according to the embodiment of the present invention.

In the same embodiment of the present invention, the differential expression of the GNMT mRNA and protein was observed in all of the tested sets each consisting of a tumor tissue and a normal tissue from the same subject. Moreover, it is surprisingly found that the GNMT gene is either not expressed or expressed at a considerably low level in hepatic tumorous cell lines.

In another aspect, the present invention provides a method of detecting abnormalities of cells by determining the expression levels of GNMT in the cells.

In another embodiment of the present invention, one of the full-length GNMT cDNA fragments obtained in the present invention was subcloned into a prokaryotic expression vector and a RP of GNMT was produced in $E.\ coli$ cells which have been transformed with the recombinant expression vector. The produced RP was readily purified and then split to release the free GNMT protein. The GNMT protein as obtained was then confirmed by Western blotting using antibodies against the protein.

In another aspect, the present invention provides the GNMT protein encoded by the full-length cDNA fragments of GNMT obtained according to the present invention, the production thereof and the antibodies raised therefor.

In another embodiment of the present invention, a series of immunohistochemical analyses were conducted for tumorous and non-tumorous liver tissues from HCC patients by using the antibodies according to the present invention which were raised against the GNMT protein. The observations in the histochemical analyses showed that the GNMT protein could be found in a large quantity within normal liver cells but hardly found within cancer cells.

In another embodiment of the present invention, one of the full-length GNMT cDNA fragments obtained in the present invention was subcloned into a eukaryotic expression vector, such as a vector driven by a promoter from cytomegalovirus. Cultures of malignant cell lines were transfected with the recombinant eukaryotic vector. The transfectants were subcloned to be stable populations by drug selection. The stable transfectants were characterized by in vitro tumorgenicity assessments. The cells of malignant sources which can stably express the GNMT after transfection of infection were inoculated into SCID mice for further in vivo assessments of the tumorgenicity thereof. The in vivo and in vitro assessments respectively showed that the tumorgenicity of the malignant cells were reduced by delivering the GNMT protein into the cells and the progress to cancer in the tested animals inoculated with the malignant cells expressing the GNMT protein was prevented.

In another aspect, the present invention provides a method of correcting abnormalities of cells having decreased level of GNMT by delivering GNMT into the cells.

BRIEF DESCRIPTION OF THE DRAWINGS

FIGS. 4a and 4b depict the nucleotide sequences of a full-length human GNMT cDNA clone 9-1-2 (SEQ ID NO:1) and an isoform GNMT cDNA clone 6-2 (SEQ ID NO:3), respectively, and the predicted amino acid sequences thereof (SEQ ID NOS:2 and 4, respectively). The nucleotides or amino acid residues which are different from those reported by Ogawa et al. (infra) are printed in bold form.

FIG. 5 is a schematic illustration of the construction of the plasmid pGEX-GNMT.

in FIG. 6a, lanes 1 and 2: commassie blue staining of a SDS-polacrylamide gel containing lysates from E. coli BL21 harboring pGEX-GNMT before and after IPTG induction; lanes 3 and 4: the unbounded and the eluent of the bounded fractions obtained according to the glutathione-agarose-bead-purification procedure; in FIG. 6b, lanes 5 and 7: using pre-immunized rabbit sera; lanes 6 and 8: using post-immunized rabbit sera. Molecular weight markers are labeled at the left margin of each of FIGS. 6a and 6b.

FIG. 8 is a schematic illustration of the construction of the plasmid pCMV-GNMT.

DETAILED DESCRIPTION OF THE PREFERRED EMBODIMENTS

Figure 1:
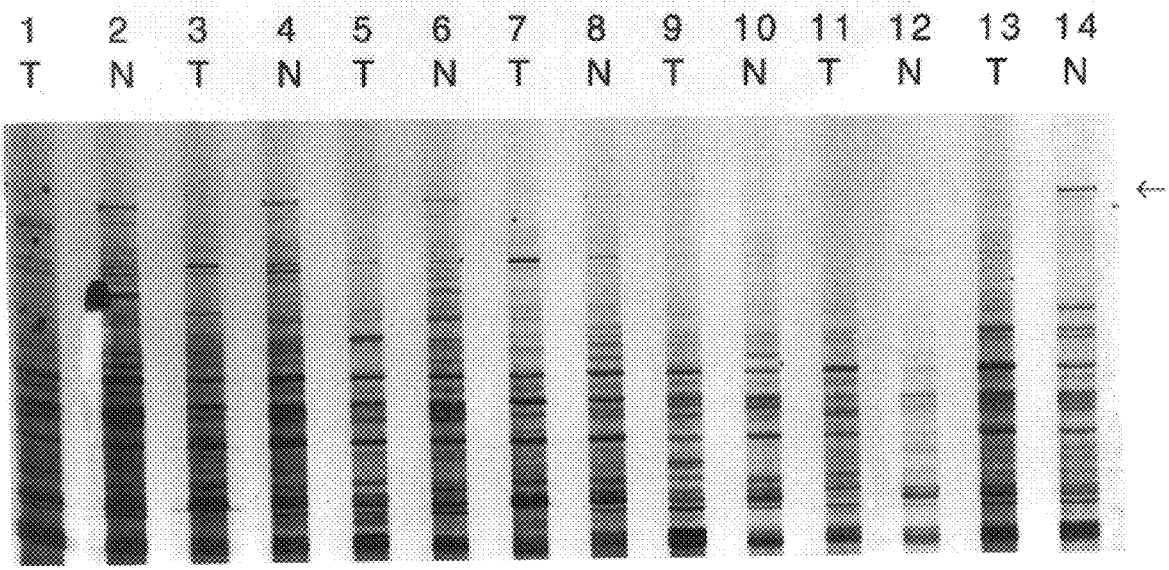
FIG. 1 shows the results of mRNA differential display of human tumorous (T) and non-tumorous (N) liver tissues from patients with hepatocellular carcinoma (HCC), lanes 1 and 2: patient HCC-1; lanes 3 and 4: patient HCC-5; lanes 5 and 6: patient HCC-7; lanes 7 and 8: patient HCC-8; lanes 9 and 10: patient HCC-9; lanes 11 and 12: patient HCC-14; and lanes 13 and 14: patient HCC-20.

The present invention provides a method of detecting abnormalities of cells having decreased level of GNMT. The present invention further provides a method of correcting the abnormalities of cells.

Those documents in the prior art cited hereinbefore and hereinafter are incorporated into the present invention for reference.

GNMT is an intracellular enzyme which catalyzes the synthesis of sarcosine from glycine. Through this enzyme, glycine receives a methyl group from S-adenosylmethionine (SAM) and becomes sarcosine, which can be subsequently oxidized to become glycine again by sarcosine dehydrogenase. The latter reaction will generate energy and release one carbon unit from SAM. GNMT thus plays a key role in regulating the ratio of SAM to S-adenosylhomocysteine (SAH). The properties of rat liver GNMT, such as its activity being fluctuated and correlated with the level of methionine in the diet and its inducibility with a methionine-rich diet, suggest that it also plays a crucial role in regulating tissue concentration of SAM and metabolism of methionine (Ogawa, H. et al., J. Biol. Chem., 257:3447–3452, 1982). However, GNMT was found to be merely responsible for the metabolism of 20% of total metabolized methionine in vivo (Case et al., J. Nutr. 106: 1721–1736, 1976), but this protein is abundant in liver of mature rats or mice, almost 1% to 3% of the total soluble proteins in liver (Heady et al., J. Biol. Chem., 248:69–72, 1973). Therefore, the GNMT protein may exert other important physiological functions, one of which was found to be identical to a folate-binding protein purified from rat liver cytosol (Cook, R. J. et al., Proc. Natl. Acad. Sci. USA, 81:3631–3634, 1984). Recently, Raha et al. (J. Biol. Chem., 269:5750–5756) proved that GNMT is the 4 S polycyclic aromatic hydrocarbon-binding protein which interacts with $5^1$-flanking regions of the cytochrome P4501A1 gene (CYP1A1).

Furthermore, as GNMT is the most abundant and efficient methyltransferase in hepatocytes, the activity of GNMT may influence other methyltransferases, e.g., the activity of tRNA methyltransferase can be blocked by GNMT (Kerr et al., J. Biol. Chem., 247:4248–4252, 1972). Results from various laboratories have indicated that lipotropic compounds, such as SAM and its precursors: methionine, choline and betaine, can prevent the development of liver tumors induced by various carcinogens in a rat or mouse model. Due to the findings that GNMT is tightly associated with the SAM level in liver cells and its enzyme activity may be activated by SAM, the GNMT may involve the chemopreventive pathway way of liver cancer (Pascale et al., Anticancer Res., 13:1341–1356, 1993).

According to the differential display method designed by Liang et al. (supra), it is feasible to display all the mRNAs present in a cell by differential display assays (reverse transcription-polymerase chain reaction, RT-PCR) with 80 different primer combinations. However, it was very time-consuming to perform so many reactions. In addition, when the method was conducted for studying the gene expression of human cancers, many cDNA fragments amplified in the tumorous samples may originate from normal cells contaminated in the tissues, which may complicate the analyses. The present invention provides a solution of the above problems by using more than one pair of tumorous and non-tumorous tissues and 12 primer pairs of the 80 primer combinations which were selected based on the relative numbers of cDNA bands able to be amplified by each of the primer pairs.

A cDNA fragment indicating distinct mRNA expression patterns between tumorous and non-tumorous liver tissues was isolated. The cDNA fragment was found to be in homology (97.7%) with the human GNMT gene. A full-length cDNA fragment of GNMT and an isoform thereof were obtained after screening a cDNA library and then the sequences thereof were determined.

It is also surprisingly found in the present invention that the GNMT gene is either not expressed or expressed at a considerably low level in hepatic tumorous cell lines. The in vivo expression of the GNMT gene may be monitored by using, e.g., nucleic acid hybridization. In general, the more stringent conditions are employed in the hybridization analyses, the more specific results are rendered. The stringencies of conditions can be estimated as described in, e.g., *Molecular Cloning-A Laboratory Manual*, 2nd edition, (eds.) J. Sambrook et al., 1989, pp9.47–9.58 and readily chosen by those persons skilled in the art.

Therefore, the present invention provides a method of detecting abnormalities of cells by determining the expression of GNMT in the cells.

Furthermore, one of the full-length GNMT cDNA fragments obtained in the present invention was subcloned into a eukaryotic expression vector. The recombinant expression vector expressing the GNMT protein was delivered into cultures of malignant cell lines and the stable populations of the treated cultures were obtained by drug selection. The in vivo and in vitro characterizations of those treated cultures respectively showed that the tumorgenicity of the malignant cells were reduced by delivering the GNMT protein into the cells and the progress to cancer in the tested animals inoculated with the malignant cells expressing the GNMT protein was prevented.

Moreover, the abnormal cells, e.g., cells with deficiency/decreased level of GNMT, of a subject may be utilized for in vitro transfection with the recombinant vector expressing the GNMT protein according to the present invention, followed by repositing those transfected cells to the subject. A minimum amount of normal cells able to maintain the vital functions thereof can be thus achieved in the subject.

A GNMT cDNA fragment obtained in the present invention may be operably introduced into a non-pathogenic eukaryotic virus, such as a modified adenovirus, by using existing techniques. To this end, the recombinant non-pathogenic virus expressing the GNMT protein has a variety of applications in correcting abnormalities of cells. For instance, under proper construction, the non-pathogenic recombinant virus may be administered to abnormal cells in a subject, e.g., through injection into a solid tumor. The abnormal cells in the subject may be corrected at the presence of a therapeutically effective amount of the GNMT protein in the cells which is resulted from the infection with the non-pathogenic recombinant virus.

Therefore, the present invention further provides a method of correcting abnormalities of cells having decreased level of GNMT by delivering GNMT into the cells.

All of the documents or publications as recited in the text are incorporated herein be reference.

Further details of this invention are illustrated in the following examples.

EXAMPLES

Example 1

Identification of the Differential Expression of the GNMT Gene Between Tumorous and Non-tumorous Cells 1.1. Sources of Tissue Specimens There are seven human hepatic tumors and their corresponding normal liver tissues, and a normal liver tissue without the tumorous counterpart thereof, provided by the Veterans General Hospital, Taipei, Taiwan, R.O.C. Informed consent was obtained from all the eight patients (designated HCC-1, -5, -7, -8, -9, -14, -20 and -24). All the specimens were frozen immediately after surgical resection and stored in liquid nitrogen before the test. All tumorous and non-tumorous tissue specimens were confirmed by pathologic examination.

1.2 RNA Extraction and mRNA Differential Display

Total RNA from the tissue specimens were purified by Ultras-pec™ RNA extraction kit (BioTecx, Houston, Tex.). The extracted RNA was treated with RNase-free DNase I (GenHunter, Brookline, Mass.) and then used for mRNA differential display with reagents from an RNAmap™ kit (GenHunter). The mRNA differential display was conducted as described by Liang et al. (supra). The primers used in the assay included 4 "$T_{12}MN$" primers and 20 arbitrary oligonucleotide primers (AP-1 to AP-20) (GenHunter). AmpliTaq DNA polymerase and alpha-[$^{35}S$]-dATP as used were available from Perkin-Elmer (Norwalk, Conn.) and New England Nuclear (Boston, Mass.), respectively.

RNAs extracted from tumorous and non-tumorous specimens from the patient HCC-20 were used to screen for suitable primer pairs from 80 combinations which can be used for mRNA differential display. The criteria of selection were based on the relative numbers of cDNA which could be amplified.

TABLE 1

The Primer Combinations Used for Differential Display

| | Arbitrary Primers (AP-1 to AP-20) | |
|---|---|---|
| $T_{12}MN$ | primers amplifying more bands | primers having differentially expressed bands in three sets of normal and tumorous specimens |
| $T_{12}MA$ | Ap-1, -11 and -18 | AP-18 |
| $T_{12}MT$ | Ap-1, -15 and -18 | AP-15 |

TABLE 1-continued

The Primer Combinations Used for Differential Display

Arbitrary Primers (AP-1 to AP-20)

| $T_{12}MN$ | primers amplifying more bands | primers having differentially expressed bands in three sets of normal and tumorous specimens |
|---|---|---|
| $T_{12}MG$ | Ap-1, -11 and -18 | AP-18 |
| $T_{12}MC$ | Ap-1, -5 and -16 | AP-16 |

As shown in Table 1, 12 combinations of primer pairs were chosen to amplify three pairs of normal and tumor specimens from HCC patients. Among them, four pairs of primers were able to amplify differentially expressed cDNA bands in all the three pairs of specimens. The differential display pattern was further confirmed by seven pairs of tumorous and non-tumorous specimens from HCC patients. As illustrated in FIG. 1, the differential display using the primers $T_{12}MC$ and AP-16 for the four patients HCC-1, -5, -7 and -8 shows a cDNA band (arrow) present only in the normal liver tissues (lanes 2, 4, 6 and 8) but not in their HCC tissue counterparts (lanes 1, 3, 5 and 7). The cDNA band was found both in the normal and tumor specimens of the patient HCC-9 (lanes 9 and 10). For the patient HCC-20, although the cDNA band was found in the tumor specimen (lane 13), its intensity was much lower than that found in the non-tumorous tissue (lane 14).

1.3. Band Recovery, Amplification and Characterization of the cDNA Fragment

The cDNA band showing differential expression as described above was cut out from the dried gel and the cDNA band was eluted by boiling the gel in 100 μl $H_2O$ for 15 minutes. The cDNA fragment was recovered by ethanol precipitation in the presence of 0.3 M NaOAC and glycogen (0.1 μg/μl). The precipitated DNA was redissolved in 10 μl of $H_2O$ and 4 μl of it was re-amplified in a reaction volume of 40 μl by PCR with the same primers ($T_{12}MC$ and AP-16). The resultant cDNA fragment of 0.8 kilobase (kb) designated 7N1 was then subcloned into a pGEM-T vector (Promega, Madison, Wis.) and its nucleotide sequence was determined by di-deoxynucleotide sequencing method (Toneguzzo et al., Biotechniques, 6:460–469, 1988) using Sequenase version 2.0 kit (United States Biochemistry) with T7 and Sp6 primers (Promega). The sequencing data was analyzed by using the BLAST software program, as described by Stephen, F. A., J. Mol. Biol., 215:403–410, 1990.

The 7N1 cDNA insert has 818 base pairs and it shares 98.7% nucleotide sequence homology with a cDNA of the human glycine N-methyltransferase (GNMT) gene (data not shown).

1.4. Northern Blot Analysis

For Northern blot analysis, 20 μl of RNA of each specimen was electrophoresed in a 1.2% agarose gel with formaldehyde and transferred to a nitrocellulose membrane (Strategene, La Jolla, Calif.). The cDNA probe was labeled with α-[$^{32}P$]-dCTP (Amersham, Buckinghamshire, England) by using Redi-Prime kit (Amersham). The conditions for pre-hybridization and hybridization reactions were as follows: 5×SSPE, 5×Denhardt's, 50% formamide, salmon sperm DNA (100 μg per ml) and 0.1% SDS without or with 1×10$^6$ cpm per ml of the radiolabelled probe at 42° C. for 2 and 24 hours, respectively. The membrane was washed twice with washing buffer A (2×SSC and 0.1% SDS) at room temperature each for 15 minutes, then with buffer B (0.1% SSC, 0.1% SDS) at 50° C. for 60 minutes. The washed membrane was autoradiographed with Kodak XAR-5 film (Kodak, Cambridge, Mass.) at −80° C.

Figure 2:
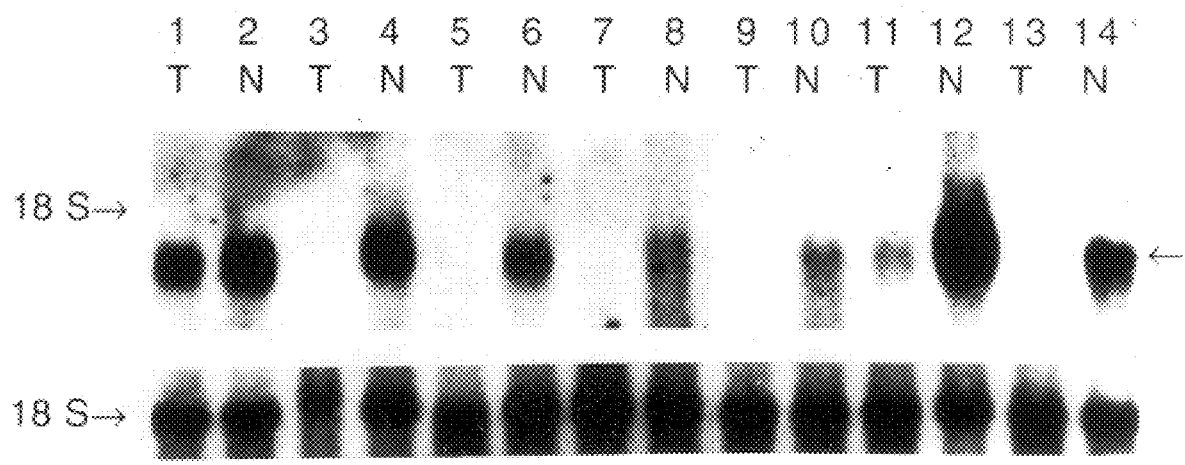
FIG. 2 shows the results of Northern blotting results of GNMT expression in human tumorous (T) and non-tumorous (N) liver tissues from patients with HCC, lanes 1 and 2: patient HCC-1; lanes 3 and 4: patient HCC-5; lanes 5 and 6: patient HCC-7; lanes 7 and 8: patient HCC-8; lanes 9 and 10: patient HCC-9; lanes 11 and 12: patient HCC-14; and lanes 13 and 14: patient HCC-20. The 18S ribosome RNA (rRNA) from each specimen was also probed. The relative locations of 18S rRNA are indicated at the right margin of this figure.

To confirm the results of mRNA differential display, 7N1 DNA was radio-labeled as a probe for Northern blot analyses. As shown in FIG. 2, a 1.4 kb mRNA of the putative GNMT gene was detected in the non-tumorous liver tissue specimens of all the 7 HCC patients (the even-number lanes), while it was absent in the tumor specimens from five patients: HCC-5, -7, -8, 14, and -24 (lanes 3, 5, 7, 11, and 15). For patients HCC-1 and HCC-20, the expression levels of GNMT gene in the liver tumors (lanes 1 and 13) were much lower than that in the non-tumorous specimens (lanes 2 and 14).

The results of the Northern blot analyses of the expression of GNMT in the tumorous tissues from HCC patients are consistent with that of mRNA differential display (see FIG. 2).

1.5. Liver cDNA Library Screening

A human liver cDNA library constructed by using phage ZAP-II vector system was obtained from the Institute of Genetics, National Yang-Ming University, Taipei, R.O.C. The liver tissues used for the construction of the cDNA library were from a healthy male Taiwanese who had died in a traffic accident. The library contains 1.1×10$^6$ independent clones. The titer of the library was approximately 1×10$^9$ pfu per ml. In the primary screening, 1×10$^6$ pfu of phages were spread on ten 15-cm plates at high density (100,000 pfu/plate), and the replica filters were screened with $^{32}$P-labeled 7N1 DNA. All positive plaques were picked up and resuspended in 1 ml SM buffer [0.01 M NaCl, 0.01 M MgSO$_4$, Tris HCl (pH 7.5) and 0.01% gelatin] with one drop of chloroform. These phage suspensions were titrated and plated at 100–1000 pfu/plate for secondary screening and final recovery. The phage clones screened were further converted into phagemid forms by using a helper phage in a non-suppressing bacterial host system-ExAssist™ Interference-Resistant Helper Phage with XLOLR strain (Strategene).

When the 7N1 cDNA fragment was used as a probe to screen for its cDNA in the Taiwanese normal liver cDNA library as mentioned above, nine positive clones were obtained after screening 1×10$^6$ phages.

1.6. Determination of the Nucleotide Sequence of the GNMT cDNA Clones

The nucleotide sequences of the phagemids of the nine positive clones were analyzed by using dideoxynucleotide sequencing method as described by Toneguzzo et al. (supra) with 12 different primers which including T3 and T7 primers (Strategene) and 10 GNMT sense (S) and anti-sense (A) primers. The GNMT primers were designed according to the GNMT cDNA sequence reported by Ogawa et al. (Comp. Biochem. Physiol., 106b: 601–611, 1993) as follows:

S1, 5'-TGTGGCAGCTGTATATCGGA-3' (89–108)(SEQ ID NO:5);
S2, 5'-GAGGGCTTCAGTGTGACGAG-3' (232–251)(SEQ ID NO:6);
S4, 5'-TGTGCACCCCCAGGGAAGAA-3' (559–578) (SEQ ID NO:7);
S5, 5'-CTACCCACACTGTCTGGCAT-3' (732–751)(SEQ ID NO:8);
S6, 5'-CCTCTGCCCAGGCACTGCTA-3' (907–926)(SEQ ID NO:9);
A1, 5'-TGCTCTAGAGGCTGGCCCTG-3' (983–964)(SEQ ID NO:10);

A2, 5'-GGGTTTGTAAGGCTTGAAGT-3' (828–809)(SEQ ID NO:11);
A3, 5'-CCTGGGGGTGCACAGCCTGT-3' (572–553)(SEQ ID NO:12);
A4, 5'-CTTGTCGAAGGCGGGCTCGT-3' (330–311)(SEQ ID NO:13); and
A5, 5'-AAGCAGCCATGCCTTGTACT-3' (150–131)(SEQ ID NO:14).

A positive clone designated as 9-1-2 was selected for further analysis. As shown in FIG. 4, the index "0" is the start of the transcribed region. Clone 9-1-2 (FIG. 4a) has 1096 nucleotides, with the first ATG codon leading an open reading frame extending to the termination codon located 295th triplets downstream. At the 3' end, a poly(A) sequence was observed. In comparison with the GNMT cDNA sequence reported by Ogawa et al. (supra), clone 9-1-2 has 4 nucleotides differences in the coding region which results in the amino residue 24 changed from glutamic acid to aspartic acid (FIG. 4a).

Another positive clone designated as 6-2 was also subjected to further analysis. It has 1113 nucleotides with the first ATG codon leading an open reading frame extending to the termination codon located 293 triplets downstream (FIG. 4b). At 3' end, a poly(A) sequence was observed. In comparison with the GNMT cDNA sequence reported by Ogawa et al. (supra), clone 6-2 has a dramatic change of nucleotide sequence encoding its N-terminal 15 amino acids except the initiation codon (FIG. 4b). Therefore, clone 6-2 only shared 94.9% amino acid sequence homology with the reported GNMT sequence.

1.7. Confirmation of the cDNA by PCR and Sequencing

To confirm the genetic changes found in the GNMT cDNA clone, cDNAs were prepared from RNAs extracted from normal liver tissues of 3 patients. The cDNAs were used as templates for PCR with primers S7 and A1. The nucleotide sequence of primer S7 was 5'-TGGCCAGGATGGGTGTCCTG-3' (690–709)(SEQ ID NO:15). PCRs were performed in a 50 μl reaction containing Taq polymerase buffer (50 mM KCl, 0.01% gelatin and 10 mM Tris buffer, pH 8.3, 1 mM $MgCl_2$), 100 ng genomic DNA, 0.2 mM of each deoxynucleotide triphosphate, 25 pmol of each primer, 0.5 unit of AmpliTaq DNA polymerase and 5% dimethyl sulfoxide. PCR conditions were recommended by the manufacturer, except that the $MgCl_2$ was 2 mM and the primers were 0.5 mM, as suggested by Innis et al. (eds.), "Optimization of PCRs-In PCR Protocols", Academic Press, San Diego, Calif. pp. 3–12. The PCR products were analyzed by electrophoresis on 2% agarose gels, and then subject to nucleotide sequence analyses by using a Dye Terminator Cycle Sequencing Core Kit on a DNA sequencer (Applied Biosystems model 373, Perkin Elmer Cetus Corp., Foster City, Calif.) with both primers as mentioned above.

The divergence of the nucleotide sequences of clone 9-1-2 has been confirmed by further sequencing the GNMT cDNA fragments from the other 3 Taiwanese patients.

Example 2
Determination of the GNMT Expression in Tumorous and Non-tumorous Cell Lines
2.1. Cell Lines and Culture Cell lines used in this study were: 4 HCC cell lines [HuH 7 (Nakabayashi et al., Cancer Res., 42:3858–3862, 1982), HA22T/VGH (Chang et al., Molec. Cell Biol., 3:1133–1137, 1983), Hep 3B, and SK-Hep-1 (Aden et al., Nature, 282:615–616, 1976; Fogh et al., J. Natl. Cancer Inst., 41:209–214, 1977)]; 2 hepatoblastoma cell lines [HuH 6 (Nakabayashi et al., supra) and Hep G2 (Aden et al., supra)]. These cells were cultured in Dulbecco's modified Eagle's medium (DMEM, GIBCO BRL, Grand Island, N.Y.) with 10% heat-inactivated fetal bovine serum (HyClone, Logan, Utah), penicillin (100 IU per ml), streptomycin (100 μg per ml), fungizone, (2.5 mg per ml), and L-glutamine (2 mM) in a humidified incubator with 5% $CO_2$.

2.2. RNA Extraction and Northern Blot Analyses

Total RNA from the cultures of the HCC and hepatoblastoma cell lines were purified respectively by Ultraspec™ RNA extraction kit (BioTecx, Houston, Tex.). The extracted RNA was treated with RNase-free DNase I (GenHunter, Brookline, Mass.).

For Northern blot analysis, 20 μl of RNA of each type of cultures was electrophoresed in a 1.2% agarose gel with formaldehyde and transferred to a nitrocellulose membrane (Strategene, La Jolla, Calif.). The cDNA probe was labeled with α-[$^{32}$p]-dCTP (Amersham, Buckinghamshire, England) by using Redi-Prime kit (Amersham). The conditions for pre-hybridization and hybridization reactions were as follows: 5×SSPE, 5×Denhardt's, 50% formamide, salmon sperm DNA (100 μg per ml) and 0.1% SDS without or with $1\times10^6$ cpm per ml of the radiolabeled probe at 42° C. for 2 and 24 hours, respectively. The membrane was washed twice with washing buffer A (2×SSC and 0.1% SDS) at room temperature each for 15 minutes, then with buffer B (0.1% SSC, 0.1% SDS) at 50° C. for 60 minutes. The washed membrane was autoradiographed with Kodak XAR-5 film (Kodak, Cambridge, Mass.) at −80° C.

Figure 3:
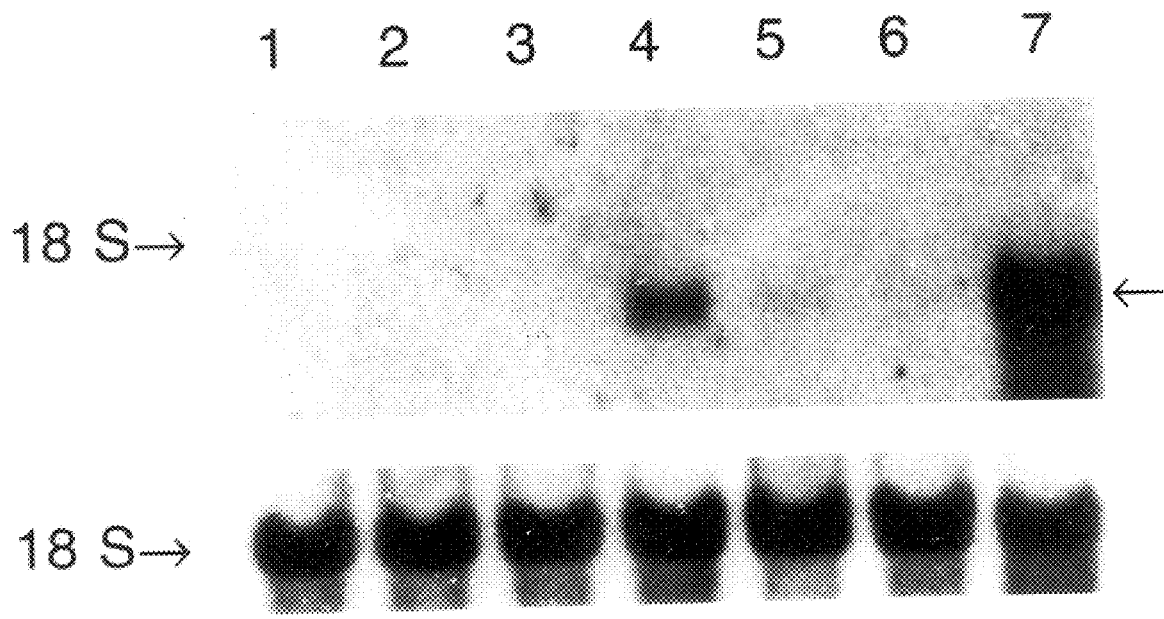
FIG. 3 shows the results of Northern blotting results of GNMT expression in human HCC and hepatoblastoma cell lines, lane 1: HA22T/VGH; lane 2: SK-Hep 1; lane 3: Hep3B; lane 4: Hep G2; lane 5: HuH-6; lane 6: HuH-7; and lane 7: HCC-24. The 18S rRNA from each culture was also probed. The relative locations of 28S and 18S rRNA were indicated at the right margin of this figure.

The results showed that the expression of the putative GNMT gene diminished completely in 4 HCC cell lines, i.e., HA22T/VGH, SK-Hepl, Hep 3B and HuH-7 (FIG. 3, lanes 1, 2, 3, and 6). Furthermore, in comparison with the normal control of the non-tumorous specimen from patient HCC-24 (lane 7), the level of gene expression decreased significantly in each of the two hepatoblastoma cell lines: HepG2 (lane 4) and HuH-6 (lane 5).

The results of the Northern blot assays on the expression of GNMT in the human HCC lines are quite consistent with that of mRNA differential display (see FIG. 3). Although the gene expression of GNMT was still detectable in the two hepatoblastoma cell lines rather than being diminished completely in the HCC cell lines, there is a distinct difference between the GNMT mRNA quantities in the normal and the hepatoblastoma cells.

Example 3
Purification and Identification of the GNMT Protein Produced in E. coli Cells
3.1. Construction of a pGEX-GNMT Plasmid The full-length GNMT cDNA fragment of 1.2 kb was cleaved from a plasmid pBluescript-GNMT-9-1-2 containing the clone 9-1-2 by using SmaI and XhoI restriction enzymes (Boehringer Mannheim), and this 1.2 kb DNA fragment was ligated to the vector pGEX-KG (Guan et al., Anal. Biochem., 192:262–267, 1991) previously digested with SmaI and XhoI restriction enzymes, such that the GNMT cDNA fragment could be linked in frame to the GST gene, as illustrated in FIG. 5. The resultant plasmid designated as pGEX-GNMT was confirmed by using the dideoxynucleotide sequencing method as described by Toneguzzo et al., supra (data not shown) and then transformed into E. coli strain BL21.

3.2. Expression and Purification of a GNMT Recombinant Protein

The expression of the plasmid pGEX-GNMT can be induced using isopropyl-beta-thiogalactopyranoside (IPTG) and hence a GST-GNMT RP was produced. To induce the RP, E. coli BL21 cells which harbor plasmid pGEX-GNMT were grown at 37° C. in LB broth containing 50 ug/ml ampicillin, and then the production of the GST-GNMT RP was induced in BL21 cells using IPTG. The produced RP was pprified by using glutathione-Sepharose 4B beads (Pharmacia, Uppsala, Sweden), as described by Guan et al. (supra). The bounded GST-GNMT RP was eluted from the glutathione-Sepharose 4B beads by using 5 mM reduced glutathione buffer (Sigma). Thrombin (Sigma) digestion method was also used to purify GNMT RP from the bead-bounded GST-GNMT RP as described by Guan et al. supra. Both the GST-GNMT and GNMT RPs were quantified using Pierce BCA protein assay reagent (Pierce, Rockford, Ill.) and further analyzed by 12.5 SDS-polyacrylamide minigel (Bio-Rad Laboratories, Richmond, Calif.) electrophoresis.

Figures 6A, 6B:
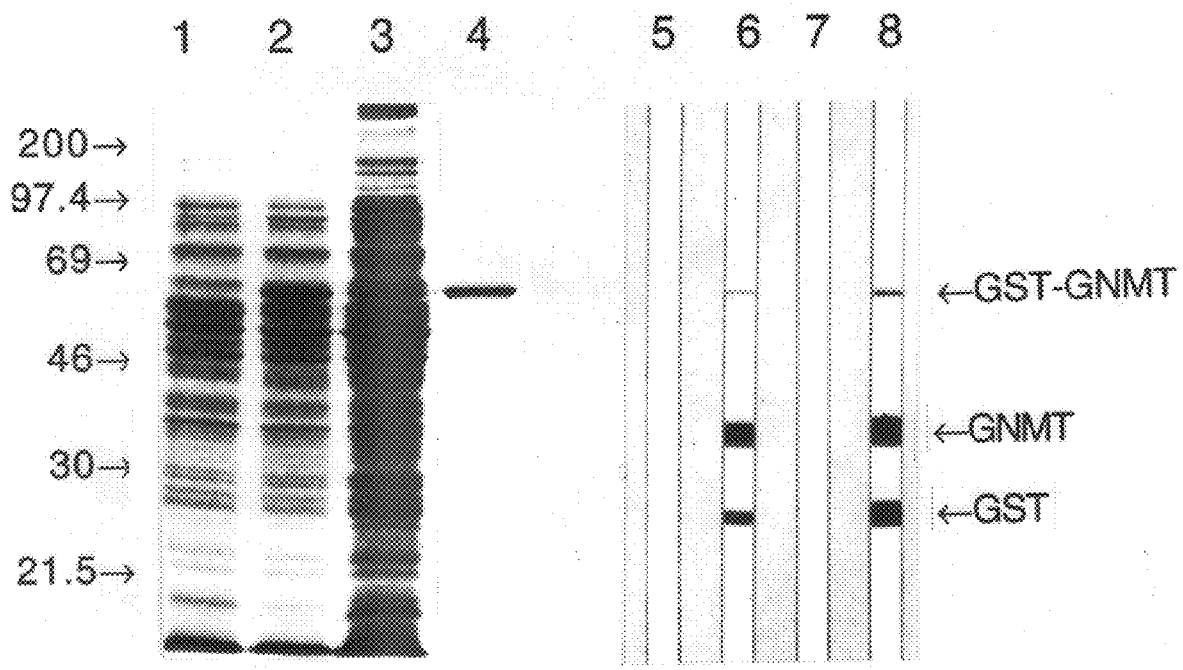
FIGS. 6a and 6b show the identifications of a GST-GNMT RP in E. coli system by electrophoresis and Western blot analysis.

For analysis of the synthesized RP, 10 μl of aliquots of both the IPTG-induced and non-induced bacterial pellets dissolved in sample buffer [0.1M dithiothreitol (DTT), 2% SDS, 0.08M Tris, pH 6.8, 10% glycerol and 0.2% bromophenol blue], were analyzed by using electrophoresis on a 12.5% SDS-polyacrylamide gel, and the induced GST-GNMT RP was visualized by staining with Coomassie brilliant blue 250. As shown in FIG. 6a, a protein of about 63.7 kd could be present in the IPTG-induced bacterial lysates (lane 2). The expressed RP was further purified by using glutathione-Sephrarose 4B beads (FIG. 6a, lane 4).

3.3. Preparation of Rabbit Antisera Against GNMT RP

To raise rabbit antibodies against GNMT RP, purified GST-GNMT RP was mixed with Freund complete (for the initial immunization) or incomplete (for the booster injections) adjuvant (Sigma) and the resultant mixture was used as immunogen to inoculate 8-week-old NEW rabbits (150–200 μg RP per rabbit) subcutaneously. The rabbits received booster injections every 3 weeks after the initial injection for four times with additional doses of the same RP. Rabbit sera were collected before the immunization and 1 week after each injection. All sera were heat-inactivated at 56° C. for 30 minutes and stored at −20° C.

3.4. Western Blot Assay (WB)

For the analysis of purified RPs, the GNMT protein and the production of rabbit anti-GNMT antibodies, about 100 μg RP in 50 μl eluent underwent thrombin (Sigma) digestion as described by Guan et al. (supra) and then the reaction products were subject to SDS-12.5% polyacrylamide minigel electrophoresis. The procedures of the WB have been described by Chen, et al., J. Immunol., 147:2368–2376, 1991.

As shown in the Western blot result of FIG. 6b, both rabbit antisera had anti-GNMT and anti-GST antibody reactivities (lanes 6 and 8). The GNMT protein produced in an *E. coli* system has the molecular weight of about 32 kilodaltons (kd) as determined by the SDS-PAGE, which is quite compatible with the protein predicted by the cDNA 9-1-2.

3.5. Immunohistochemical Studies

Normal and tumor tissues from 3 HCC patients were used for immunohistochemical studies with the rabbit anti-GNMT antibodies as obtained in Example 3.3. Formalin-fixed, OCT-embedded frozen tissue blocks were sliced into 6 μm-thick sections and stained with rabbit pre-immunized sera or anti-GNMT sera at ⅟50, ⅟100, ⅟200, ⅟500 and ⅟1,000 dilutions. Tissue sections were immersed in 3% hydrogen peroxide for 5 minutes to abolish the endogenous peroxidase reaction. After washing in PBS, these sections were immersed in 0.5% NP-40 for 5 minutes and then incubated with rabbit sera overnight. Subsequently, they were reacted with biotinylated antibody and peroxidase-labeled streptavidin (DAKO, Danmark) for 15 minutes each. These slides were further incubated with 3,3'-diaminobenzidine tetrahydrochloride solution for color reaction and hematoxylin was used for counter staining.

Figure 7:
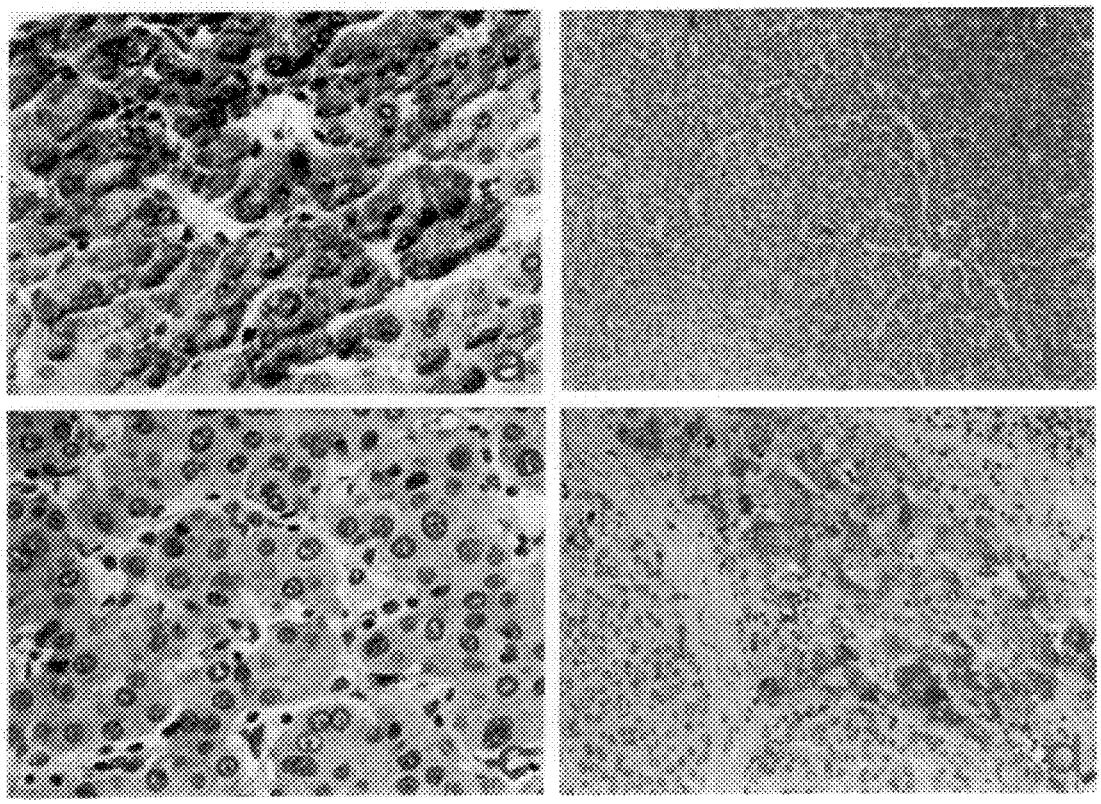
FIG. 7 shows microscopic photographs of immunohistochemical analyses of HCC cryostat sections exposed to rabbit anti-GNMT and visualized by a labeled streptavidine-biotin method. Pathological sections of non-tumorous (FIG. 7a) and tumorous tissues (FIGS. 7b and 7c) from an HCC patient J-96-1415 were examined in the analyses. A section of tumorous tissue from another HCC patient J95-3707 stained by rabbit anti-GNMT antibodies at 40×manifestation (FIG. 7d).

As shown in FIG. 7, the GNMT protein was expressed abundantly in the cytoplasms of normal liver cells from a patient J96-1415 (see FIG. 7a), while the protein was not expressed in almost all the cancer cells from the same patient (see FIGS. 7b and 7c). In the study of tissue sections from another patient J95-3707, the GNMT protein was only expressed within the normal liver cells which were clustered in a small island surrounded by liver tumor nodules without GNMT staining (FIG. 7d). There was no GNMT staining by using a rabbit control (preimmunized) serum (data not shown).

Example 4

The Effects on Tumorous Cells by Delivering the GNMT Protein into the Cells 4.1. Construction of Eukaryotic Vector pCMV-GNMT and Generation of Recombinant Adenovirus AdGNMT5

To construct a eukaryotic vector, the plasmid pGEX-GNMT obtained in above Example 3.1 was digested with SmaI and SalI restriction enzymes (Boehringer Mannheim) and the free full-length GNMT cDNA fragment was obtained. This 1.2-kb DNA fragment was ligated to the vector pBK-CMV previously digested with the same restriction enzymes, as illustrated by FIG. 8. The resultant plasmid was designated as pCMV-GNMT.

Figure 9:
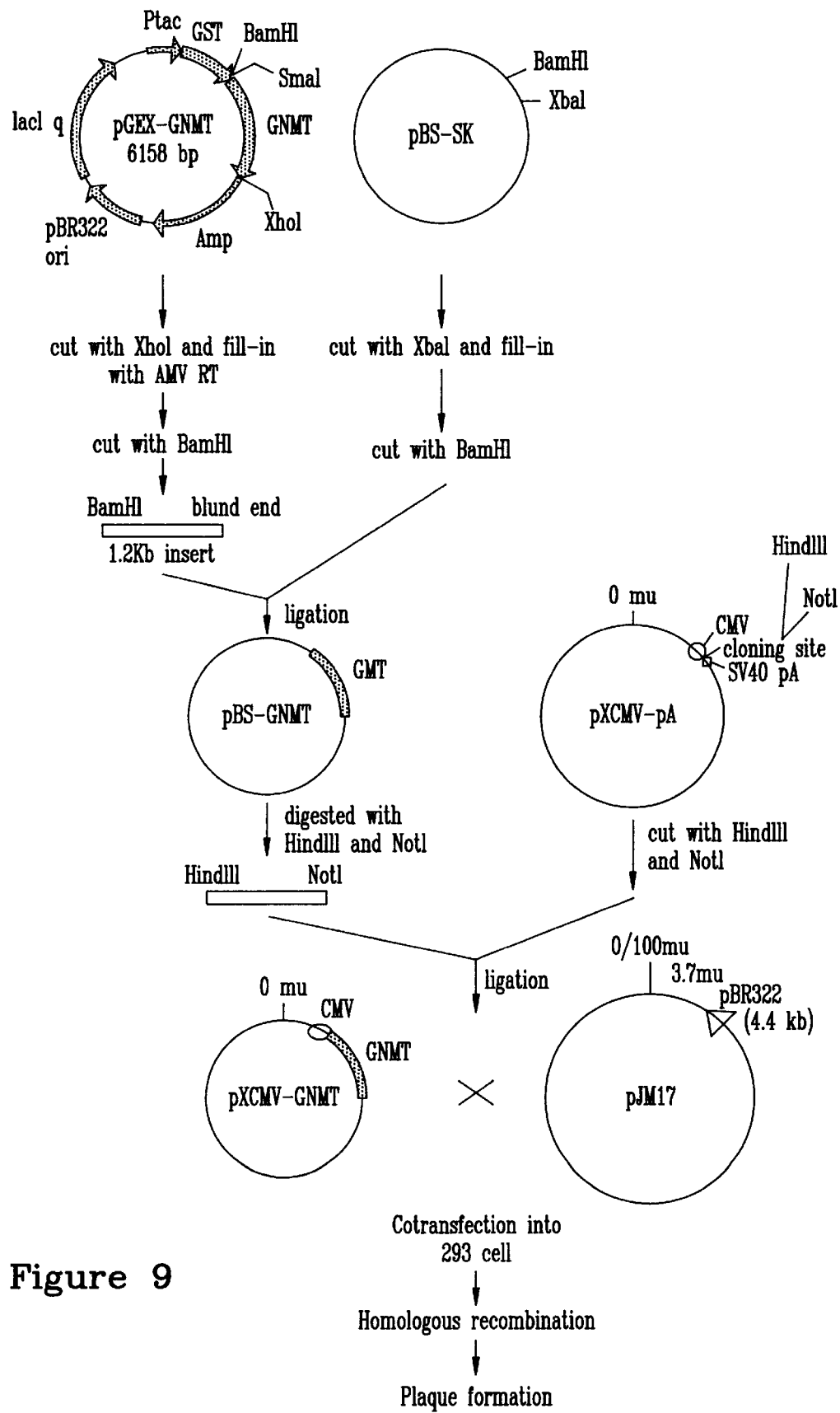
FIG. 9 is a schematic illustration of the generation of a recombinant adenovirus designated as AdGNMT5 which contains the GNMT cDNA.

A recombinant adenovirus harboring GNMT cDNA according to the present invention was created as follow. As shown in FIG. 9, the full-length GNMT cDNA fragment was obtained from pGEX-GNMT of Example 3.1 and then subcloned into a plasmid pBSK (Stratagene Co.) whereby a plasmid pBS-GNMT was obtained. The same cDNA fragment from the plasmid PBS-GNMT was further subcloned into pXCMVCAM (Kleinerman, D. et al., Cancer Res., 55:2831–2836, 1995). The resultant plasmid and an adenoviral genome, pJM17 (cf. Kleinerman et al., supra), were co-transfected into 293 (Graham et al., J. Gen. Virol., 36:59–74, 1977) cells and then a recombinant adenovirus designated as AdGNMT5 was yielded. The recombinant virus AdGNMT5 carrying cDNA coding for GNMT is able to be applied to approaches of gene therapy.

4.2. Transfection

Before transfection, cells were seeded in 6-well plates ($4.5 \times 10^5$ cells per well) and then neomycin sulfate (G418) was added to achieve the graded final concentrations (0, 0.5, 1.0, 2.0, 4.0 and 5.0, respectively). The drug concentration which can extinguish cells in 3 to 7 days was chosen for subsequent drug selection of the transfectants. The addition of G418 to the final concentration 500 μg/ml is preferred.

Cells were plated into plates in 10 cm diameter ($5-8 \times 10^6$ cells per plate). After 18 to 24 hours, the cells would grow to about 80% confluence. The plasmid pCMV-GNMT was mixed with transfectase in preferred ratios (1:15 for HA22T and 1:6 for Hep3B). The mixture was allowed to be homogeneous and then incubated at room temperature for 15 minutes. After the DNA-liposome complex formed, the complex was mixed gently with 5 ml OPTI-MEMI culture medium without serum. The mixture was added into each of the plates with cells plated therein and then was distributed uniformly by slightly shaking. The transfection plates were incubated at 37° C. and 5% $CO_2$ for 6 hours and then 6 ml fresh DMEM medium containing heat-inactivated fetal bovine serum (HyClone, Logan, Utah) was added into each plate for further incubation. After 18 to 24 hours, the medium in each plate was changed to DMEM-10 [DMEM medium containing 10% fetal calf serum (HyClone, Logan, Utah)] and the transfectants attached to the plates were expanded and cultured in DMEM-10 containing G418 (final concentration is 500 μg/ml) for drug selection such that stable clones would be obtained.

4.3. Anchorage-independent Colony Formation

The transfectants survived after drug selection were tripsinized and centrifuged. Any conditioned media were removed by decanting the supernatant. The cells were resuspended in DMEM-10 and counted. Serial dilutions of an adequate amount of cells were conducted with methocel-medium (complete DMEM containing 1.3% methocel from Sigma) in triplicates and then added in plates each containing medium with 0.9% agar ($10^5$, $10^4$, $10^3$, or $10^2$ cells per plate). Four ml of methocel-medium was added to each plate every seventh day and the colonies formed were counted in the third week of incubation. In this assay, colonies each containing more than 20 cells were counted and recorded. The results are presented in Table 2.

TABLE 2

Results of Colony Formation of Liver Cancer Cell Lines with or without Treatments

| Cell lines | Colony Formation (%) |
|---|---|
| HA22T (C) | 52.3 |
| HA22T (G) | 41.1 |
| Hep3B (C) | 31.7 |
| Hep3B (G) | 26.5 |

(C): cell lines transfected with the vector pCMV;
(G): cell lines transfected with pCMV-GNMT As shown in Table 2, in comparison with the colony formation percentage of either HA22T or Hep3B cells transfected with vector pCMV alone, cells transfected with pCMV-GNMT had a lower percentage of colony formation. Therefore, GNMT is effective in reducing tumorgenicity.

4.5. Serum Requirement Assay

Figure 10:
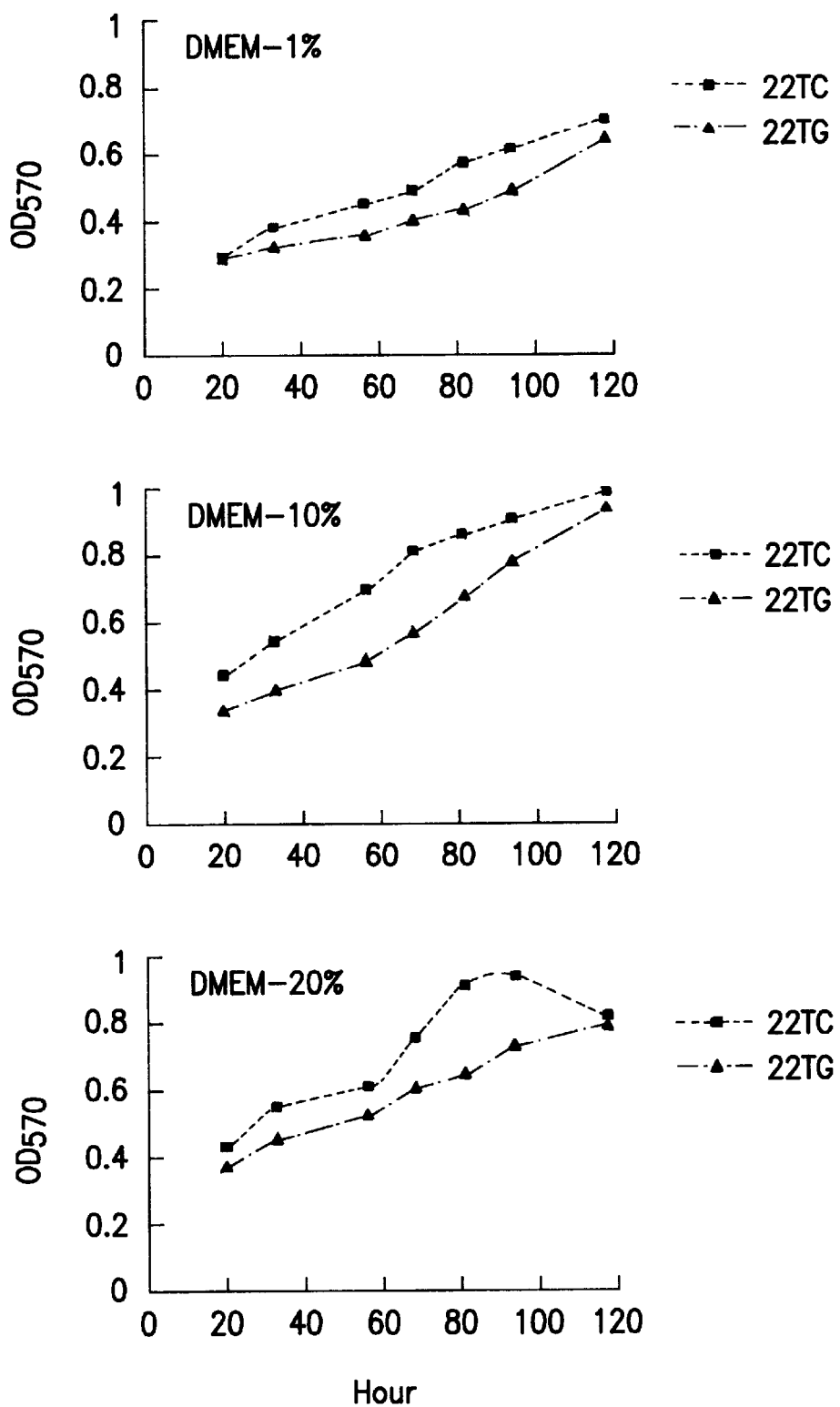
FIG. 10 shows the growth profiles of HA22T cells transfected with pCMV-GNMT (22TG) or pCMV (22TC) in DMEM media supplemented with different concentrations (1%, 10% and 20%) of heat-inactivated fetal bovine serum.

Six groups of cells, i.e., HA22T and Hep3B cells which were not transfected, transfected by the vector pBK-CMV only and by the recombinant vector pCMV-GNMT, were cultured in 96-well plates ($3\times10^4$ cells per well) in triplicate. Those plates were incubated at 37° C. and 5% $CO_2$ for 20 hours. The serum requirement assay was performed in batches every twelve hours. For this assay, 10 μl (5 mg/ml) of 3-[4,5-dimethylthiazol-2-yl]-2,5-diphenyl tetrazolium bromide (MTT) in phosphate buffered saline (PBS) was added into each of the wells and a batch of plates was incubated as per the same conditions for further 4 hours. One hundred μl of solubilization buffer (10% SDS in 0.01 M HCl) was added to each of the wells and then the batch of plates was incubated for further 20 hours. Optical absorbance was measured at a wave length of 570 nm. The growth profiles of HA22T cells transfected with either pCMV (22TC) or pCMV-GNMT (22TG), which were cultivated in media containing different concentrations (1%, 10% and 20%) of fetal calf serum (HyClone, Logan, Utah), are shown in FIG. 10.

The results show that HA22T cells transfected with pCMV-GNMT (22TG) had lower growth rate in comparison with the cells transfected with pCMV alone (22TC). Therefore, the expression of GNMT has suppressive effect on the liver cancer cells.

4.6. Severe Combined Immunodeficient (SCID) Mice Inoculation Test

Before this test, the SCID animals were subject to a serum immunoglobin test. Goat anti-mouse Ig Ab (Sigma) was diluted with coating buffer (Carbonate/bicarbonate, 0.01 M, pH 9.5) to the concentration of 1 μg/ml. Into each well of 96-well plates 100 μl of the diluent was added and stored at room temperature for 16 hours. The plates were incubated at room temperature for 2 hours after 200 μl of blocking buffer (3% BSA in PBS) was added into each of the wells. The wells were washed five times with PBS and then a secondary antibody (horseradish peroxidase-conjugated sheep anti-mouse antibody) was added into them. The wells were washed five times again with PBS after incubation for one hour. The substrate O-phenylene diamine (Sigma) was added into each of the wells and then the plates were incubated for 30 minutes, followed by the addition of 10% $H_2SO_4$ to halt the reaction. Optical absorbance was measured at a wave length of 492 nm.

The SCID animals to be tested were divided into two groups. Each group has three mice. Three animals of the first group were subcutaneously injected at two loci with $5\times10^6$ HA22T cells per mouse, wherein the cells were transfected with pBK-CMV and pCMV-GNMT, respectively. The animals of the second group were treated as the experimental design for the first group except the cell number was $1\times10^6$. After injection, the size of the tumor originated from the injected cancer cells in each mouse was metered and recorded weekly. The results are shown in Table 3.

TABLE 3

Subcutaneous Tumors of SCID mice Induced by Inoculating HA22T Cells Transfected with pCMV or pCMV-GNMT

| Cell Numbers | | Volume of tumors (mm³) | |
|---|---|---|---|
| being inoculated | No. | HA22TC | HA22TG |
| $5 \times 10^6$ | 1-1 | 378 | 350 |
| | 1-2 | 180 | 48 |
| | 1-3 | 765 | 180 |
| | average | 441 ± 298 | 193 ± 151 |
| $1 \times 10^6$ | 2-1 | 75 | 32 |
| | 2-2 | ND | ND |
| | 2-3 | 315 | 48 |
| | average | 195 | 40 |

(C): cells transfected with the vector pCMV;
(G): cells transfected with pCMV-GNMT;
ND: not detected As shown in Table 3, the size of tumors found in SCID mice inoculated with the vector pCMV is significantly greater than the size of tumors of SCID mice inoculated with the plasmid pCMV-GNMT. This result shows the suppression of malignant tumors by introducing GNMT protein into the tumor cells wherein said protein has not been expressed or expressed at a considerably low level.

Although the invention has been explained in relation to its preferred embodiment, it is to be understood that many other possible modifications and variations can be made without departing from the spirit and scope of the invention as hereinafter claimed.

I claim:

1. A method of detecting an abnormality of cells comprising comparing the level of glycine N-methyltransferase (GNMT) with cells not having the abnormality, the abnormal cells having a decreased level of GNMT.

2. The method according to claim 1, wherein the abnormality is hepatocellular carcinoma.

3. The method according to claim 1, wherein the abnormality is heptoblastoma.

* * * * *

UNITED STATES PATENT AND TRADEMARK OFFICE
CERTIFICATE OF CORRECTION

PATENT NO. : 5,994,093
DATED : November 30, 1999
INVENTOR(S) : Yi-Ming A. Chen

It is certified that error appears in the above-identified patent and that said Letters Patent is hereby corrected as shown below:

<u>Title page,</u>

Page 6, immediately underneath the heading "BRIEF DESCRIPTION OF THE DRAWINGS" please insert the following paragraph:

-- The file of this patent contains at least one drawing executed in color. Copies of this patent with color drawing(s) will be provided by the Patent and Trademark Office upon request and payment of necessary fee. --.

Page 6,
line 26, please replace "Figure 4 depicts" with -- Figures 4a and 4b depict --.

Signed and Sealed this

Eighteenth Day of September, 2001

*Attest:*

NICHOLAS P. GODICI
*Attesting Officer*     *Acting Director of the United States Patent and Trademark Office*

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
       (A) LENGTH: 1097 base pairs
       (B) TYPE: nucleic acid
       (C) STRANDEDNESS: double
       (D) TOPOLOGY: linear (ii) MOLECULE TYPE: cDNA to mRNA (iii) HYPOTHETICAL: NO (iv) ANTI-SENSE: NO (vi) ORIGINAL SOURCE:
       (C) INDIVIDUAL ISOLATE: nucleotide sequence encoding
           a human glycine N-methyltransferase protein (vii) IMMEDIATE SOURCE:
       (B) CLONE: 9-1-2

(ix) FEATURE:
       (B) LOCATION: 11..885

(xi) SEQUENCE DESCRIPTION: SEQ ID NO:1:

```
GGCACGAGGG ATG GTG GAC AGC GTG TAC CGG ACC CGC TCC CTG              43
           Met Val Asp Ser Val Tyr Arg Thr Arg Ser Leu
            1               5                  10

GGG GTG GCG GCC GAA GGG CTC CCG GAC CAG TAC GCG GAC GGG             85
Gly Val Ala Ala Glu Gly Leu Pro Asp Gln Tyr Ala Asp Gly
            15                  20                  25

GAG GCG GCG CGC GTG TGG CAG CTG TAT ATC GGA GAC ACC CGC            127
Glu Ala Ala Arg Val Trp Gln Leu Tyr Ile Gly Asp Thr Arg
        30                  35

AGC CGC ACC GCC GAG TAC AAG GCA TGG CTG CTT GGG CTG CTG            169
Ser Arg Thr Ala Glu Tyr Lys Ala Trp Leu Leu Gly Leu Leu
 40              45                  50

CGC CAG CAC GGC TGC CAG CGG GTG CTC GAC GTA GCC TGT GGC            211
Arg Gln His Gly Cys Gln Arg Val Leu Asp Val Ala Cys Gly
     55                  60                  65

ACT GGG GTG GAC TCC ATT ATG CTG GTG GAA GAG GGC TTC AGT            253
Thr Gly Val Asp Ser Ile Met Leu Val Glu Glu Gly Phe Ser
             70                  75                  80

GTG ACG AGT GTG GAT GCC AGT GAC AAG ATG CTG AAG TAT GCA            295
Val Thr Ser Val Asp Ala Ser Asp Lys Met Leu Lys Tyr Ala
             85                  90                  95

CTT AAG GAG CGC TGG AAC CGG CGG CAC GAG CCC GCC TTC GAC            337
Leu Lys Glu Arg Trp Asn Arg Arg His Glu Pro Ala Phe Asp
                100                 105

AAG TGG GTC ATC GAA GAA GCC AAC TGG ATG ACT CTG GAC AAA            379
Lys Trp Val Ile Glu Glu Ala Asn Trp Met Thr Leu Asp Lys
110             115                 120

GAT GTG CCC CAG TCA GCA GAG GGT GGC TTT GAT GCT GTC ATC            421
Asp Val Pro Gln Ser Ala Glu Gly Gly Phe Asp Ala Val Ile
        125                 130                 135

TGC CTT GGA AAC AGT TTC GCT CAC TTG CCA GAC TGC AAA GGG            463
Cys Leu Gly Asn Ser Phe Ala His Leu Pro Asp Cys Lys Gly
            140                 145                 150

GAC CAG AGT GAG CAC CGG CTG GCG CTG AAA AAC ATT GCG AGC            505
Asp Gln Ser Glu His Arg Leu Ala Leu Lys Asn Ile Ala Ser
```

```
ATG GTG CGG GCA GGG GGC CTA CTG GTC ATT GAT CAT CGC AAC       547
Met Val Arg Ala Gly Gly Leu Leu Val Ile Asp His Arg Asn
            170                 175

TAC GAC CAC ATC CTC AGT ACA GGC TGT GCA CCC CCA GGG AAG       589
Tyr Asp His Ile Leu Ser Thr Gly Cys Ala Pro Pro Gly Lys
180                 185                 190

AAC ATC TAC TAT AAG AGT GAC TTG ACC AAG GAC GTC ACA ACA       631
Asn Ile Tyr Tyr Lys Ser Asp Leu Thr Lys Asp Val Thr Thr
    195                 200                 205

TCA GTG CTG ATA GTG AAC AAC AAG GCC CAC ATG GTG ACC CTG       673
Ser Val Leu Ile Val Asn Asn Lys Ala His Met Val Thr Leu
        210                 215                 220

GAC TAT ACG GTG CAG GTG CCG GGG GCT GGC CAG GAT GGC TCT       715
Asp Tyr Thr Val Gln Val Pro Gly Ala Gly Gln Asp Gly Ser
            225                 230                 235

CCT GGC TTG AGT AAG TTC CGG CTC TCC TAC TAC CCA CAC TGT       757
Pro Gly Leu Ser Lys Phe Arg Leu Ser Tyr Tyr Pro His Cys
                240                 245

CTG GCA TCC TTC ACG GAG CTG CTC CAA GCA GCC TTC GGA GGT       799
Leu Ala Ser Phe Thr Glu Leu Leu Gln Ala Ala Phe Gly Gly
250                 255                 260

AAG TGC CAG CAC AGC GTC CTG GGC GAC TTC AAG CCT TAC AAG       841
Lys Cys Gln His Ser Val Leu Gly Asp Phe Lys Pro Tyr Lys
    265                 270                 275

CCA GGC CAA ACC TAC ATT CCC TGC TAC TTC ATC CAC GTG CTC       883
Pro Gly Gln Thr Tyr Ile Pro Cys Tyr Phe Ile His Val Leu
        280                 285                 290

AAG AGG ACA GAC TGAGTGTGGC CTCAGCTCCC ACAAGCCTCT              925
Lys Arg Thr Asp
            295

GCCCAGGCAC TGCTAGGCTC TGTCTGGAAG ATGGGGACCA GCAGCCCCAC        975

ACCAGGGCCA GCCTCTAGAG CAGACTACAG CTGGGGTGCA GGGATGTGGG       1025

TTCCACAGAC GGAAGGGTAA ACAATATAGT CTTTTTCAGT TCCTGCAAAA       1075

AAAAAAAAAA AAAAAAAAAA AA                                     1097
```

(2) INFORMATION FOR SEQ ID NO:2:

(i) SEQUENCE CHARACTERISTICS:
        (A) LENGTH: 295 amino acids
        (B) TYPE: amino acid
        (D) TOPOLOGY: linear (ii) MOLECULE TYPE: protein (vi) ORIGINAL SOURCE:
        (C) INDIVIDUAL ISOLATE: predicted amino acid
            coding sequence of SEQ ID NO:1

(xi) SEQUENCE DESCRIPTION: SEQ ID NO:2:

```
        Met Val Asp Ser Val Tyr Arg Thr Arg Ser Leu Gly
          1               5                  10

Val Ala Ala Glu Gly Leu Pro Asp Gln Tyr Ala Asp Gly Glu Ala
            15                  20                  25

Ala Arg Val Trp Gln Leu Tyr Ile Gly Asp Thr Arg Ser Arg Thr
            30                  35                  40

Ala Glu Tyr Lys Ala Trp Leu Leu Gly Leu Leu Arg Gln His Gly
            45                  50                  55

Cys Gln Arg Val Leu Asp Val Ala Cys Gly Thr Gly Val Asp Ser
            60                  65                  70
```

```
Ile Met Leu Val Glu Glu Gly Phe Ser Val Thr Ser Val Asp Ala
         75                  80                  85

Ser Asp Lys Met Leu Lys Tyr Ala Leu Lys Glu Arg Trp Asn Arg
         90                  95                 100

Arg His Glu Pro Ala Phe Asp Lys Trp Val Ile Glu Glu Ala Asn
        105                 110                 115

Trp Met Thr Leu Asp Lys Asp Val Pro Gln Ser Ala Glu Gly Gly
        120                 125                 130

Phe Asp Ala Val Ile Cys Leu Gly Asn Ser Phe Ala His Leu Pro
        135                 140                 145

Asp Cys Lys Gly Asp Gln Ser Glu His Arg Leu Ala Leu Lys Asn
        150                 155                 160

Ile Ala Ser Met Val Arg Ala Gly Gly Leu Leu Val Ile Asp His
        165                 170                 175

Arg Asn Tyr Asp His Ile Leu Ser Thr Gly Cys Ala Pro Pro Gly
        180                 185                 190

Lys Asn Ile Tyr Tyr Lys Ser Asp Leu Thr Lys Asp Val Thr Thr
        195                 200                 205

Ser Val Leu Ile Val Asn Asn Lys Ala His Met Val Thr Leu Asp
        210                 215                 220

Tyr Thr Val Gln Val Pro Gly Ala Gly Gln Asp Gly Ser Pro Gly
        225                 230                 235

Leu Ser Lys Phe Arg Leu Ser Tyr Tyr Pro His Cys Leu Ala Ser
        240                 245                 250

Phe Thr Glu Leu Leu Gln Ala Ala Phe Gly Gly Lys Cys Gln His
        255                 260                 265

Ser Val Leu Gly Asp Phe Lys Pro Tyr Lys Pro Gly Gln Thr Tyr
        270                 275                 280

Ile Pro Cys Tyr Phe Ile His Val Leu Lys Arg Thr Asp
        285                 290                 295

(2) INFORMATION FOR SEQ ID NO:3:

(i) SEQUENCE CHARACTERISTICS:
        (A) LENGTH: 1113 base pairs
        (B) TYPE: nucleic acid
        (C) STRANDEDNESS: double
        (D) TOPOLOGY: linear (ii) MOLECULE TYPE: cDNA to mRNA (iii) HYPOTHETICAL: NO (iv) ANTI-SENSE: NO (vi) ORIGINAL SOURCE:
         (C) INDIVIDUAL ISOLATE: nucleotide sequence encoding
             a human glycine N-methyltransferase protein (vii) IMMEDIATE SOURCE:
          (B) CLONE: 6-2

(ix) FEATURE:
         (B) LOCATION: 24..902

(xi) SEQUENCE DESCRIPTION: SEQ ID NO:3:

GGCACGAGGA ACAGCAGTTG AAC ATG GGT CAG TCG GTC CTG AGA              44
                         Met Gly Gln Ser Val Leu Arg
                          1               5

GAT GGG CGA GCG CCG TTC CGA AGG CTC CCG GAC CAG TAC GCG            86
Asp Gly Arg Ala Pro Phe Arg Arg Leu Pro Asp Gln Tyr Ala
         10                  15                  20
```

| | |
|---|---|
| GAC GGG GAG GCG GCG CGC GTG TGG CAG CTG TAT ATC GGA GAC<br>Asp Gly Glu Ala Ala Arg Val Trp Gln Leu Tyr Ile Gly Asp<br>                  25                      30                    35 | 128 |
| ACC CGC AGC CGC ACC GCC GAG TAC AAG GCA TGG CTG CTT GGG<br>Thr Arg Ser Arg Thr Ala Glu Tyr Lys Ala Trp Leu Leu Gly<br>                  40                      45 | 170 |
| CTG CTG CGC CAG CAC GGC TGC CAG CGG GTG CTC GAC GTA GCC<br>Leu Leu Arg Gln His Gly Cys Gln Arg Val Leu Asp Val Ala<br>50                      55                      60 | 212 |
| TGT GGC ACT GGG GTG GAC TCC ATT ATG CTG GTG GAA GAG GGC<br>Cys Gly Thr Gly Val Asp Ser Ile Met Leu Val Glu Glu Gly<br>    65                      70                      75 | 254 |
| TTC AGT GTG ACG AGT GTG GAT GCC AGT GAC AAG ATG CTG AAG<br>Phe Ser Val Thr Ser Val Asp Ala Ser Asp Lys Met Leu Lys<br>        80                      85                      90 | 296 |
| TAT GCA CTT AAG GAG CGC TGG AAC CGG CGG CAC GAG CCC GCC<br>Tyr Ala Leu Lys Glu Arg Trp Asn Arg Arg His Glu Pro Ala<br>            95                      100                  105 | 338 |
| TTC GAC AAG TGG GTC ATC GAA GAA GCC AAC TGG ATG ACT CTG<br>Phe Asp Lys Trp Val Ile Glu Glu Ala Asn Trp Met Thr Leu<br>                  110                      115 | 380 |
| GAC AAA GAT GTG CCC CAG TCA GCA GAG GGT GGC TTT GAT GCT<br>Asp Lys Asp Val Pro Gln Ser Ala Glu Gly Gly Phe Asp Ala<br>120                      125                      130 | 422 |
| GTC ATC TGC CTT GGA AAC AGT TTC GCT CAC TTG CCA GAC TGC<br>Val Ile Cys Leu Gly Asn Ser Phe Ala His Leu Pro Asp Cys<br>    135                      140                      145 | 464 |
| AAA GGG GAC CAG AGT GAG CAC CGG CTG GCG CTG AAA AAC ATT<br>Lys Gly Asp Gln Ser Glu His Arg Leu Ala Leu Lys Asn Ile<br>        150                      155                      160 | 506 |
| GCG AGC ATG GTG CGG GCA GGG GGC CTA CTG GTC ATT GAT CAT<br>Ala Ser Met Val Arg Ala Gly Gly Leu Leu Val Ile Asp His<br>            165                      170                  175 | 548 |
| CGC AAC TAC GAC CAC ATC CTC AGT ACA GGC TGT GCA CCC CCA<br>Arg Asn Tyr Asp His Ile Leu Ser Thr Gly Cys Ala Pro Pro<br>                  180                      185 | 590 |
| GGG AAG AAC ATC TAC TAT AAG AGT GAC TTG ACC AAG GAC GTC<br>Gly Lys Asn Ile Tyr Tyr Lys Ser Asp Leu Thr Lys Asp Val<br>190                      195                      200 | 632 |
| ACA ACA TCA GTG CTG ATA GTG AAC AAC AAG GCC CAC ATG GTG<br>Thr Thr Ser Val Leu Ile Val Asn Asn Lys Ala His Met Val<br>    205                      210                      215 | 674 |
| ACC CTG GAC TAT ACG GTG CAG GTG CCG GGG GCT GGC CAG GAT<br>Thr Leu Asp Tyr Thr Val Gln Val Pro Gly Ala Gly Gln Asp<br>        220                      225                      230 | 716 |
| GGC TCT CCT GGC TTG AGT AAG TTC CGG CTC TCC TAC TAC CCA<br>Gly Ser Pro Gly Leu Ser Lys Phe Arg Leu Ser Tyr Tyr Pro<br>            235                      240                  245 | 758 |
| CAC TGT CTG GCA TCC TTC ACG GAG CTG CTC CAA GCA GCC TTC<br>His Cys Leu Ala Ser Phe Thr Glu Leu Leu Gln Ala Ala Phe<br>                  250                      255 | 800 |
| GGA GGT AAG TGC CAG CAC AGC GTC CTG GGC GAC TTC AAG CCT<br>Gly Gly Lys Cys Gln His Ser Val Leu Gly Asp Phe Lys Pro<br>260                      265                      270 | 842 |
| TAC AAG CCA GGC CAA ACC TAC ATT CCC TGC TAC TTC ATC CAC<br>Tyr Lys Pro Gly Gln Thr Tyr Ile Pro Cys Tyr Phe Ile His<br>    275                      280                      285 | 884 |
| GTG CTC AAG AGG ACA GAC TGAGTGTGGC CTCAGCTCCC ACAAGCCTCT<br>Val Leu Lys Arg Thr Asp<br>            290 | 932 |

```
GCCCAGGCAC TGCTAGGCTC TGTCTGGAAG ATGGGGACCA GCAGCCCCAC         982

ACCAGGGCCA GCCTCTAGAG CAGACTACAG CTGGGGTGCA GGGATGTGGG        1032

TTCCACAGAC GGAAGGGTAA ACAATATAGT CTTTTTCAGT TCCTGAAAAA        1082

AAAAAAAAAA AAAAAAAAAA AAAAAAAAAA A                            1113
```

(2) INFORMATION FOR SEQ ID NO:4:

(i) SEQUENCE CHARACTERISTICS:
        (A) LENGTH: 293 amino acids
        (B) TYPE: amino acid
        (D) TOPOLOGY: linear (ii) MOLECULE TYPE: protein (vi) ORIGINAL SOURCE:
        (C) INDIVIDUAL ISOLATE: predicted amino acid
            coding sequence of SEQ ID NO:3

(xi) SEQUENCE DESCRIPTION: SEQ ID NO:4:

```
                    Met Gly Gln Ser Val Leu Arg Asp
                                     5

Gly Arg Ala Pro Phe Arg Arg Leu Pro Asp Gln Tyr Ala Asp Gly
         10                  15                  20

Glu Ala Arg Val Trp Gln Leu Tyr Ile Gly Asp Thr Arg Ser
 25                  30                  35

Arg Thr Ala Glu Tyr Lys Ala Trp Leu Leu Gly Leu Leu Arg Gln
         40                  45                  50

His Gly Cys Gln Arg Val Leu Asp Val Ala Cys Gly Thr Gly Val
 55                  60                  65

Asp Ser Ile Met Leu Val Glu Glu Gly Phe Ser Val Thr Ser Val
 70                  75                  80

Asp Ala Ser Asp Lys Met Leu Lys Tyr Ala Leu Lys Glu Arg Trp
 85                  90                  95

Asn Arg Arg His Glu Pro Ala Phe Asp Lys Trp Val Ile Glu Glu
 100                 105                 110

Ala Asn Trp Met Thr Leu Asp Lys Asp Val Pro Gln Ser Ala Glu
 115                 120                 125

Gly Gly Phe Asp Ala Val Ile Cys Leu Gly Asn Ser Phe Ala His
 130                 135                 140

Leu Pro Asp Cys Lys Gly Asp Gln Ser Glu His Arg Leu Ala Leu
 145                 150                 155

Lys Asn Ile Ala Ser Met Val Arg Ala Gly Gly Leu Leu Val Ile
 160                 165                 170

Asp His Arg Asn Tyr Asp His Ile Leu Ser Thr Gly Cys Ala Pro
 175                 180                 185

Pro Gly Lys Asn Ile Tyr Tyr Lys Ser Asp Leu Thr Lys Asp Val
 190                 195                 200

Thr Thr Ser Val Leu Ile Val Asn Asn Lys Ala His Met Val Thr
 205                 210                 215

Leu Asp Tyr Thr Val Gln Val Pro Gly Ala Gly Gln Asp Gly Ser
 220                 225                 230

Pro Gly Leu Ser Lys Phe Arg Leu Ser Tyr Tyr Pro His Cys Leu
 235                 240                 245

Ala Ser Phe Thr Glu Leu Leu Gln Ala Ala Phe Gly Gly Lys Cys
 250                 255                 260

Gln His Ser Val Leu Gly Asp Phe Lys Pro Tyr Lys Pro Gly Gln
```

```
                265                 270                 275
Thr Tyr Ile Pro Cys Tyr Phe Ile His Val Leu Lys Arg Thr Asp
    280                 285                 290
```

(2) INFORMATION FOR SEQ ID NO:5:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 20-mer synthetic oligonucleotide (x) PUBLICATION INFORMATION:
        (A) AUTHORS: Ogawa, H
                Gomi, T
                Fujioka, M
        (B) TITLE: Mammalian Glycine N-Methyltransferase.
            Comparative Kinetic and Structural Properties of the
            Enzymes from Human, Rat, Rabbit and Pig Livers.
        (C) JOURNAL: Comp. Bichem. Physiol.
        (D) VOLUME: 106b
        (F) PAGES: 601-611
        (G) DATE: 1993
        (K) RELEVANT RESIDUES IN SEQ ID NO: FROM 1 TO 20

(xi) SEQUENCE DESCRIPTION: SEQ ID NO:5:

TGTGGCAGCT GTATATCGGA                                                  20

(2) INFORMATION FOR SEQ ID NO:6:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 20-mer synthetic oligonucleotide (x) PUBLICATION INFORMATION:
        (A) AUTHORS: Ogawa, H
                Gomi, T
                Fujioka, M
        (B) TITLE: Mammalian Glycine N-Methyltransferase.
            Comparative Kinetic and Structural Properties of the
            Enzymes from Human, Rat, Rabbit and Pig Livers.
        (C) JOURNAL: Comp. Bichem. Physiol.
        (D) VOLUME: 106b
        (F) PAGES: 601-611
        (G) DATE: 1993
        (K) RELEVANT RESIDUES IN SEQ ID NO:6: FROM 1 TO 20

(xi) SEQUENCE DESCRIPTION: SEQ ID NO:6:

GAGGGCTTCA GTGTGACGAG                                                  20

(2) INFORMATION FOR SEQ ID NO:7:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 20-mer synthetic oligonucleotide

```
    (x) PUBLICATION INFORMATION:
        (A) AUTHORS: Ogawa, H
              Gomi, T
              Fujioka, M
        (B) TITLE: Mammalian Glycine N-Methyltransferase.
            Comparative Kinetic and Structural Properties of the
            Enzymes from Human, Rat, Rabbit and Pig Livers.
        (C) JOURNAL: Comp. Bichem. Physiol.
        (D) VOLUME: 106b
        (F) PAGES: 601-611
        (G) DATE: 1993
        (K) RELEVANT RESIDUES IN SEQ ID NO:7: FROM 1 TO 20

(xi) SEQUENCE DESCRIPTION: SEQ ID NO:7:

TGTGCACCCC CAGGGAAGAA                                              20

(2) INFORMATION FOR SEQ ID NO:8:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 20-mer synthetic oligonucleotide (x) PUBLICATION INFORMATION:
        (A) AUTHORS: Ogawa, H
              Gomi, T
              Fujioka, M
        (B) TITLE: Mammalian Glycine N-Methyltransferase.
            Comparative Kinetic and Structural Properties of the
            Enzymes from Human, Rat, Rabbit and Pig Livers.
        (C) JOURNAL: Comp. Bichem. Physiol.
        (D) VOLUME: 106b
        (F) PAGES: 601-611
        (G) DATE: 1993
        (K) RELEVANT RESIDUES IN SEQ ID NO:8: FROM 1 TO 20

(xi) SEQUENCE DESCRIPTION: SEQ ID NO:8:

CTACCCACAC TGTCTGGCAT                                              20

(2) INFORMATION FOR SEQ ID NO:9:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 20-mer synthetic oligonucleotide (x) PUBLICATION INFORMATION:
        (A) AUTHORS: Ogawa, H
              Gomi, T
              Fujioka, M
        (B) TITLE: Mammalian Glycine N-Methyltransferase.
            Comparative Kinetic and Structural Properties of the
            Enzymes from Human, Rat, Rabbit and Pig Livers.
        (C) JOURNAL: Comp. Bichem. Physiol.
        (D) VOLUME: 106b
        (F) PAGES: 601-611
        (G) DATE: 1993
        (K) RELEVANT RESIDUES IN SEQ ID NO:9: FROM 1 TO 20

(xi) SEQUENCE DESCRIPTION: SEQ ID NO:9:

CCTCTGCCCA GGCACTGCTA                                              20
```

(2) INFORMATION FOR SEQ ID NO:10:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 20-mer synthetic oligonucleotide (x) PUBLICATION INFORMATION:
        (A) AUTHORS: Ogawa, H
            Gomi, T
            Fujioka, M
        (B) TITLE: Mammalian Glycine N-Methyltransferase.
            Comparative Kinetic and Structural Properties of the
            Enzymes from Human, Rat, Rabbit and Pig Livers.
        (C) JOURNAL: Comp. Bichem. Physiol.
        (D) VOLUME: 106b
        (F) PAGES: 601-611
        (G) DATE: 1993
        (K) RELEVANT RESIDUES IN SEQ ID NO:10: FROM 1 TO 20

(xi) SEQUENCE DESCRIPTION: SEQ ID NO:10:

```
TGCTCTAGAG GCTGGCCCTG                                              20
```

(2) INFORMATION FOR SEQ ID NO:11:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 20-mer synthetic oligonucleotide (x) PUBLICATION INFORMATION:
        (A) AUTHORS: Ogawa, H
            Gomi, T
            Fujioka, M
        (B) TITLE: Mammalian Glycine N-Methyltransferase.
            Comparative Kinetic and Structural Properties of the
            Enzymes from Human, Rat, Rabbit and Pig Livers.
        (C) JOURNAL: Comp. Bichem. Physiol.
        (D) VOLUME: 106b
        (F) PAGES: 601-611
        (G) DATE: 1993
        (K) RELEVANT RESIDUES IN SEQ ID NO:11: FROM 1 TO 20

(xi) SEQUENCE DESCRIPTION: SEQ ID NO:11:

```
GGGTTTGTAA GGCTTGAAGT                                              20
```

(2) INFORMATION FOR SEQ ID NO:12:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 20-mer synthetic oligonucleotide (x) PUBLICATION INFORMATION:
        (A) AUTHORS: Ogawa, H
            Gomi, T
            Fujioka, M (B) TITLE: Mammalian Glycine N-Methyltransferase.
            Comparative Kinetic and Structural Properties of the
            Enzymes from Human, Rat, Rabbit and Pig Livers.
        (C) JOURNAL: Comp. Bichem. Physiol.
        (D) VOLUME: 106b
        (F) PAGES: 601-611
        (G) DATE: 1993
        (K) RELEVANT RESIDUES IN SEQ ID NO:12: FROM 1 TO 20

(xi) SEQUENCE DESCRIPTION: SEQ ID NO:12:

CCTGGGGGTG CACAGCCTGT                                                       20

(2) INFORMATION FOR SEQ ID NO:13:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 20-mer synthetic oligonucleotide (x) PUBLICATION INFORMATION:
        (A) AUTHORS: Ogawa, H
            Gomi, T
            Fujioka, M
        (B) TITLE: Mammalian Glycine N-Methyltransferase.
            Comparative Kinetic and Structural Properties of the
            Enzymes from Human, Rat, Rabbit and Pig Livers.
        (C) JOURNAL: Comp. Bichem. Physiol.
        (D) VOLUME: 106b
        (F) PAGES: 601-611
        (G) DATE: 1993
        (K) RELEVANT RESIDUES IN SEQ ID NO:13: FROM 1 TO 20

(xi) SEQUENCE DESCRIPTION: SEQ ID NO:13:

CTTGTCGAAG GCGGGCTCGT                                                       20

(2) INFORMATION FOR SEQ ID NO:14:

(i) SEQUENCE CHARACTERISTICS:
        (A) LENGTH: 20 bases
        (B) TYPE: nucleic acid
        (C) STRANDEDNESS: single
        (D) TOPOLOGY: linear (ii) MOLECULE TYPE: DNA (synthetic)

(vi) ORIGINAL SOURCE:
        (C) INDIVIDUAL ISOLATE: 20-mer synthetic oligonucleotide (x) PUBLICATION INFORMATION:
        (A) AUTHORS: Ogawa, H
            Gomi, T
            Fujioka, M
        (B) TITLE: Mammalian Glycine N-Methyltransferase.
            Comparative Kinetic and Structural Properties of the
            Enzymes from Human, Rat, Rabbit and Pig Livers.
        (C) JOURNAL: Comp. Bichem. Physiol.
        (D) VOLUME: 106b
        (F) PAGES: 601-611
        (G) DATE: 1993
        (K) RELEVANT RESIDUES IN SEQ ID NO:14: FROM 1 TO 20

(xi) SEQUENCE DESCRIPTION: SEQ ID NO:14:

AAGCAGCCAT GCCTTGTACT                                                       20

(2) INFORMATION FOR SEQ ID NO:15:

(i) SEQUENCE CHARACTERISTICS:
        (A) LENGTH: 20 bases

```
          (B) TYPE: nucleic acid
          (C) STRANDEDNESS: single
          (D) TOPOLOGY: linear (ii) MOLECULE TYPE: DNA (synthetic)

(vi) ORIGINAL SOURCE:
          (C) INDIVIDUAL ISOLATE: 20-mer synthetic oligonucleotide (x) PUBLICATION INFORMATION:
          (A) AUTHORS: Ogawa, H
                Gomi, T
                Fujioka, M
          (B) TITLE: Mammalian Glycine N-Methyltransferase.
                Comparative Kinetic and Structural Properties of the
                Enzymes from Human, Rat, Rabbit and Pig Livers.
          (C) JOURNAL: Comp. Bichem. Physiol.
          (D) VOLUME: 106b
          (F) PAGES: 601-611
          (G) DATE: 1993
          (K) RELEVANT RESIDUES IN SEQ ID NO:15: FROM 1 TO 20

(xi) SEQUENCE DESCRIPTION: SEQ ID NO:15:

TGGCCAGGAT GGGTGTCCTG                                                    20
```